US008153116B2

(12) United States Patent
Mamoun

(10) Patent No.: US 8,153,116 B2
(45) Date of Patent: Apr. 10, 2012

(54) USE OF CONDITIONAL PLASMODIUM STRAINS LACKING AN ESSENTIAL GENE IN MALARIA VACCINATION

(75) Inventor: Choukri Ben Mamoun, Farmington, CT (US)

(73) Assignee: University of Connecticut, Farmington, CT (US)

( * ) Notice: Subject to any disclaimer, the term of this patent is extended or adjusted under 35 U.S.C. 154(b) by 214 days.

(21) Appl. No.: 12/381,326

(22) Filed: Mar. 10, 2009

(65) Prior Publication Data

US 2010/0112010 A1 May 6, 2010

Related U.S. Application Data

(63) Continuation-in-part of application No. 11/827,282, filed on Jul. 11, 2007.

(60) Provisional application No. 60/830,371, filed on Jul. 11, 2006.

(51) Int. Cl.
*A01N 63/00* (2006.01)
*A61K 39/00* (2006.01)

(52) U.S. Cl. .................. 424/93.2; 424/93.21; 424/184.1
(58) Field of Classification Search ........................ None
See application file for complete search history.

(56) References Cited

U.S. PATENT DOCUMENTS

| | | | |
|---|---|---|---|
| 4,436,727 A | 3/1984 | Ribi | |
| 4,436,728 A | 3/1984 | Ribi et al. | |
| 4,505,899 A | 3/1985 | Ribi et al. | |
| 4,505,900 A | 3/1985 | Ribi et al. | |
| 4,520,019 A | 5/1985 | Ribi et al. | |
| 4,579,945 A | 4/1986 | Schartzman et al. | |
| 4,866,034 A | 9/1989 | Ribi | |
| 4,877,611 A | 10/1989 | Cantrell | |
| 5,583,112 A | 12/1996 | Kensil et al. | |
| 5,616,491 A | 4/1997 | Mak et al. | |
| 5,912,000 A | 6/1999 | Podolski et al. | |
| 5,965,144 A | 10/1999 | Podolski et al. | |
| 5,980,912 A | 11/1999 | Podolski et al. | |
| 6,146,632 A | 11/2000 | Momin et al. | |
| 6,194,388 B1 | 2/2001 | Krieg et al. | |
| 6,207,646 B1 | 3/2001 | Krieg et al. | |
| 6,239,116 B1 | 5/2001 | Krieg et al. | |
| 6,339,068 B1 | 1/2002 | Krieg et al. | |
| 7,122,179 B2 | 10/2006 | Kappe et al. | |
| 2005/0208078 A1 | 9/2005 | Hoffman et al. | |
| 2008/0026010 A1 | 1/2008 | Mamoun | |

FOREIGN PATENT DOCUMENTS

| WO | WO-03087322 A2 | 10/2003 |
|---|---|---|
| WO | WO2004045559 | 6/2004 |
| WO | WO2005063991 | 7/2005 |

OTHER PUBLICATIONS

Witola et al (Journal of Biological Chemistry vol. 283, No. 41, pp. 27636-27643, Aug. 2008).*

Fandeur et al., "Variant- and Strain-Specific Immunity in Saimiri Infected with *Plasmodium falciparum*", Am. J. Trop. Med. Hyg. 1998, 58(2):225-231.
"WHO Expert Committee on Malaria", WHO Technical Report Series 892, i-v 2000 , 1-74.
Boleti, Haralabia et al., "Molecular Identification of the Equilibrative NBMPR-sensitive (es) Nucleoside Transporter and Demonstration of an Equilibrative NBMPR-insensitive (ei) Transport Activity in Human Erythroleukemia (K562) Cells", Neuropharmacology 1997 , vol. 36, No. 9, 1167-1179.
Carter, Nicola S. et al., "Isolation and Functional Characterization of the PfNT1 Nucleoside Transporter Gene from *Plasmodium falciparum*", The Journal of Biological Chemistry Apr. 7, 2000 , vol. 275, No. 14, 10683-10691.
Carter, Nicola S. et al., "Nucleoside transporters of parasitic protozoa", Trends in Parasitology Mar. 2001 , vol. 17, No. 3, 142-145.
Chanock, Robert M. et al., "Genetic Control of the Immune Response to a *Plasmodium falciparum* Sporozoite Vaccine and to the Circumsporozoite Protein", Vaccines87 1987 , 81-106, 117-124.
Clyde, et al., "Specificity of Protection of Man Immunized against Sporozoite-induced *falciparum* Malaria", The American Journal of the Medical Sciences 1973 , vol. 266, 398-403.
Crabb, B. S. et al., "Stable transgene expression in *Plasmodium falciparum*", Molecular and Biochemical Parasitology 1997 , 90: 131-144.
Daddona, Peter E. et al., "Human Adenosine Deaminase", The Journal of Biological Chemistry Jan. 10, 1977 , vol. 22, No. 1, 110-115.
Duraisingh, Manoj T. et al., "Negative selection of *Plasmodium falciparum* reveals targeted gene deletion by double crossover recombination", International Journal for Parasitology 2002 , 32, 81-89. El Bissati, Kamal et al., "Genetic evidence for the esstntial role of PfNT1 in the transport and utilization of xanthine, guanine, guanosine and adenine by *Plasmodium falciparum*", Molecular & Biochemical Parasitology 2008 , 161:130-139.
El Bissati, et al., "The plasma membrane permease PfNT1 is essential for purine salvage in the human malaria parasite *Plasmodium falciparum*", PNAS Jun. 13, 2006 , vol. 103(24), 9286-9291.
Ellis, R. et al., "Vaccines", Chapter 29 of "Vaccines" Plotkin.S.A et al (eds) 1998.
Fidock, David A. et al., "Cycloguanil and Its Parent Compound Proguanil Demonstrate Distinct Activities against *Plasmodium falciparum* Malaria Parasites Transformed with Human Dihydrofolate Reductase", Molecular Pharmacology 1998 , 54: 1140-1147.
Folch, Jordi et al., "A Simple Method for the Isolation and Purification of Total Lipides from Animal Tissues", The Journal of Biological Chemistry 1957 , 226, 497-509.
Francis, Susan E. et al., "Biosynthesis and Maturation of the Malaria Aspartic Hemoglobinases Plasmepsins I and II", The Journal of Biological Chemistry Jun. 6, 1997 , vol. 272, No. 23, 14961-14968.
Frevert, et al., "Arrest in the liver-a genetically defined malaria vaccine?", N Engl J Med 2005 , 352 (15), 1600-1602.

(Continued)

*Primary Examiner* — Albert Navarro
(74) *Attorney, Agent, or Firm* — Kilpatrick Townsend & Stockton LLP

(57) ABSTRACT

The present invention relates to a malaria vaccine for administration to a host, comprising an attenuated malarial parasite with a gene that has been rendered non-functional, wherein the gene, when present in naturally occurring form, encodes a protein necessary for continued in vivo survival and proliferation of the parasite and/or for infection of host red blood cells. The gene that has been rendered non-functional can be, e.g., a gene that encodes a nutrient transporter protein or a gene that encodes an enzyme involved in phospholipid biosynthesis. The invention also provides kits and methods that include such attenuated malarial parasites.

15 Claims, 15 Drawing Sheets

Figure 1:
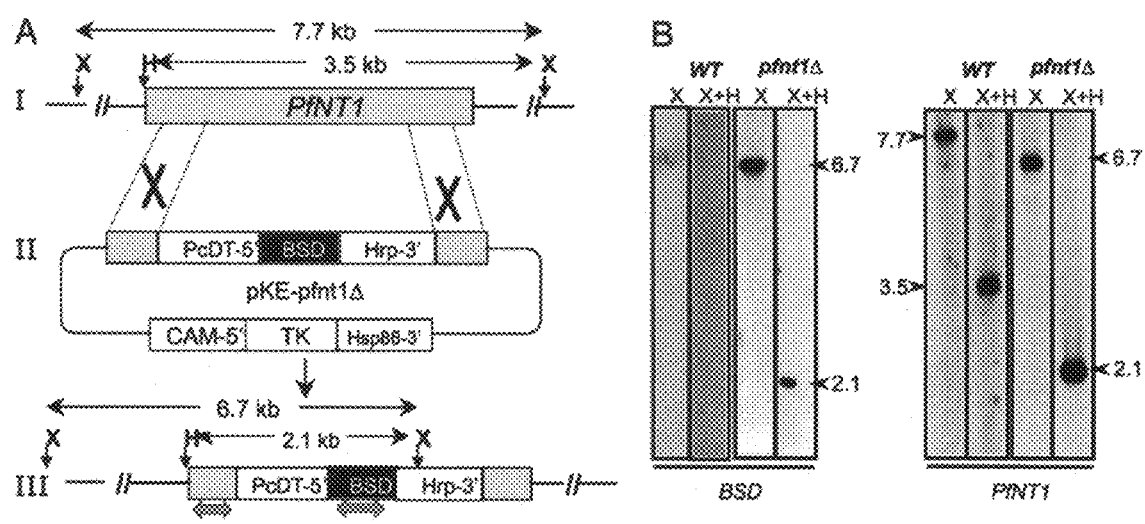

(9 of 15 Drawing Sheet(s) Filed in Color)

OTHER PUBLICATIONS

Gero, Annette M. et al., "Altered Purine Nucleoside Transport as a Target for Malaria Chemotherapy", Purine and Pyrimidine Metabolism in Man VIII 1995, 493-498.

Gero, Annette M. et al., "Purines and Pyrimidines in Malarial Parasites", Blood Cells 1990, 16, 467-484.

Gligorijevic, Bojana et al., "Spinning Disk Confocal Microscopy of Live, Intraerythrocytic Malarial Parasites. 1. Quantification of Hemozoin Development for Drug Sensitive versus Resistant Malaria", Biochemistry 2006, 45: 12400-12410.

Gligorijevic, Bojana et al., "Stage independent chloroquine resistance and chloroquine toxicity revealed via spinning disk confocal microscopy", Molecular & Biochemical Parasitology 2008, 159: 7-23.

Hayward, R. E. "*Plasmodium falciparum* phosphoenolpyruvate carboxykinase is developmentally regulated in gametocytes", Molecular & Biochemical Parasitology, vol. 107 2000, 224-240.

Hoffman, Stephen L. et al., "Protection of humans against malaria by immunization with radiation-attenuated *Plasmodium falciparum* sporozoites", Journal of Infectious Diseases Apr. 15, 2002, Chicago, IL; vol. 185(8), 1155-1164.

Holz, George G. "Lipids and the malarial parasite", Bulletin of the World Health Organization 1977, 55 (2-3): 237-248.

James, Stephanie et al., "Malaria Vaccine Development Status Report", Parasitology and International Programs Branch and Laboratory of Parasitic Diseases, National Institutes of Health 2000, 1-13.

Kirk, K. Acta Tropica Feb. 2004, vol. 89, Issue 3, 285-298.

Kirk, Kiaran "Membrane Transport in the Malaria-Infected Erythrocyte", Physiological Reviews Apr. 2001, vol. 81, No. 2, 495-537.

Krishna, Sanjeev "Science, medicine, and the future. Malaria", BMJ Sep. 20, 1997, vol. 315, 730-732.

Lambros, Chris et al., "Synchronization of *Plasmodium falciparum* Erythrocytic Stages in Culture", J. Parasitol 1979, 65 (3)418-20.

Lewis, Arthur S. et al., "Human Erythrocyte Purine Nucleoside Phosphorylase: Molecular Weight and Physical Properties", The Journal of Biological Chemistry Oct. 10, 1979, vol. 254, No. 19, 9927-9932.

Makler, M. T. et al., "Parasite Lactate Dehydrogenase as an Assay for *Plasmodium falciparum* Drug Sensitivity", Am. J. Trop. Med. Hyg. 1993, 48(6): 739-741.

Mamoun, Choukri B. et al., "A set of independent selectable markers for transfection of the human malaria parasite *Plasmodium falciparum*", Proc. Natl. Acad. Sci. USA Jul. 1999, vol. 96, 8716-8720.

Martin, Rowena E. et al., "The 'permeome' of the malaria parasite: an overview of the membrane transport proteins of *Plasmodium falciparum*", Genome Biology 2005, vol. 6, Issue 3, Article R26, R26.1-R26.22.

Matuscheswski, et al., "Vaccines against malaria—an update", FEBs Journal 2007, 274:4680-4687.

Menard, Robert "Medicine knockout malaria vaccine?", Nature Jan. 13, 2005, vol. 433(7022), 113-114.

Miller, L. H. et al., "Perspectives for malaria vaccination", Phil. Trans. R. Soc. Lond. 1984, B307: 99-115.

Mueller, A. K. et al., "Genetically modified *Plasmodium* parasites as a protective experimental malaria vaccine", Nature Jan. 13, 2005, vol. 433(7022), 164-167.

Oplinger, et al., "NIAID Tackles Malaria in Vaccine Lab", NIH record May 6, 2005, vol. LVII (9).

Parker, Marie D. et al., "Identification of a nucleoside/nucleobase transporter from *Plasmodium falciparum*, a novel target for antimalarial chemotherapy", Biochem J. 2000, 349:67-75.

Pessi, Gabriella et al., "A pathway for phosphatidylcholine biosynthesis in *Plasmodium falciparum* involving phosphoethanolamine methylation", PNAS Apr. 20, 2004, vol. 101, No. 16, pp. 6206-6211.

Pessi, Gabriella et al., "In Vivo Evidence for the Specificity of *Plasmodium falciparum* Phosphoethanolamine Methyltransferase and Its Coupling to the Kennedy Pathway", The Journal of Biological Chemistry Apr. 1, 2005, vol. 280, No. 13, 12461-12466.

Pessi, Gabriiella et al., "Pathways for phosphatidylcholine biosynthesis: targets and strategies for antimalarial drugs", Future Lipidol 2006, 1(2): 173-108.

Rager, Nicolle et al., "Localization of the *Plasmodium flaciparum* PfNT1 Nucleoside Transporter to the Parasite Plasma Membrane", The Journal of Biological Chemistry Nov. 2, 2001, vol. 276, No. 44, 41095-41099.

Santiago, T. PhD. vol. 6606B of Dissertations Abstracts International Dec. 2005, p. 2912.173 pages.

Santiago, Teresa C. et al., "The *Plasmodium falciparum* PfGatp is an Endoplasmic Reticulum Membrane Protein Important for the Initial Step of Malarial Glycerolipid Synthesis", The Journal of Biological Chemistry Mar. 5, 2004, vol. 279, No. 10, 9222-9232.

Sherman, Irwin W. "Biochemistry of *Plasmodium* (Malarial Parasites)", Microbiological Reviews Dec. 1979, vol. 43, No. 4, 453-495.

Sherman, Irwin W. "Purine and Pyrimidine Metabolism of Asexual Stages", Malaria: Parasite Biology, Pathogenesis, and Protection 1998, 177-184.

Sijwali, P. S. et al., "Gene disruption confirms a critical role for the cysteine protease falcipain-2 in hemoglobin hydrolysis by *Plasmodium falciparum*", PNAS 2004, vol. 101, 4384-4389.

Struik, et al., "Does malaria suffer from lack of memory?", Immunological Reviews 2004, vol. 201, 268-290.

Targett, Geoffrey et al., "Malaria vaccines 1985-2005: a full circle?", Trends in Parasitology, Elsevier Current Trends Nov. 1, 2005, vol. 21(11), 499-503.

Trager, William et al., "Human Malaria Parasites in Continuous Culture", Science Aug. 20, 1976, 193:673-5.

Traut, Thomas W. "Physiological concentrations of purines and pyrimidines", Molecular and Cellular Biochemistry 1994, 140:1-22.

Upston, Joanne M. et al., "Parasite-induced permeation of nucleosides in *Plasmodium falciparum* malaria", Biochimica et Biophysica Acta 1995, 1236:249-258.

Van Dijk, Melissa R. et al., "Genetically attenuated, P36p-deficient malarial sporozoites induce protective immunity and apoptosis of infected liver cells", Proceedings of the National Academy of Sciences of the United States of America Aug. 23, 2005, vol. 102(34), 12194-12199.

Vial, Henri J. et al., "*Plasmodium* Lipids: Metabolism and Function", Molecular Approaches to Malaria 2005, 327-352.

Waters, Andrew et al., "Malaria new vaccines for old?", Cell Feb. 24, 2006, vol. 124(4), 689-693.

Witola, William H. et al., "Localization of the Phosphoethanolamine Methyltransferase of the Human Malaria Parasite *Plasmodium falciparum* to the Golgi Apparatus", The Journal of Biological Chemistry Jul. 28, 2006, vol. 281, No. 30, pp. 21305-21311.

Yamada, Kenneth A. et al., "Purine Metabolizing Enzymes of *Plasmodium lophurae* and its Host Cell, the Duckling (*Anas domesticus*) Erythrocyte", Molecular and Biochemical Parasitology 1981, 2, 349-358.

Zeisel, Steven H. et al., "Choline: Needed for Normal Deelopment of Memory", Journal of the American College of Nutrition 2000, vol. 19, No. 5, 528S-531S.

Zeisel, Steven H. et al., "Normal plasma choline responses to ingested lecithin", Neurology Nov. 1980, 30: 1226-1229.

"Notice of Allowance" in U.S. Appl. No. 11/827,282, mailed Oct. 26, 2011.

* cited by examiner

SEQUENCE LISTING

```
<160> NUMBER OF SEQ ID NOS: 2

<210> SEQ ID NO 1
<211> LENGTH: 28
<212> TYPE: DNA
<213> ORGANISM: Plasmodium falciparum

<400> SEQUENCE: 1
atgactttga ttgaaaactt aaactctg                                          28

<210> SEQ ID NO 2
<211> LENGTH: 32
<212> TYPE: DNA
<213> ORGANISM: Plasmodium falciparum

<400> SEQUENCE: 2
tttggtggcc ttaaaataac cccatctttg ca                                     32
```

USE OF CONDITIONAL PLASMODIUM STRAINS LACKING AN ESSENTIAL GENE IN MALARIA VACCINATION

CROSS-REFERENCE TO RELATED APPLICATIONS

This application is a continuation-in-part of and claims priority to U.S. patent application Ser. No. 11/827,282, filed Jul. 11, 2007, which claims priority to U.S. Provisional Patent Application Ser. No. 60/830,371, filed Jul. 11, 2006. Each of the aforementioned applications is herein incorporated by reference in its entirety.

STATEMENT REGARDING FEDERALLY SUPPORTED RESEARCH

The research leading to this application was funded with United States government support under grant number AI51507 from the National Institute of Allergy and Infectious Disease, grant number AI51962 from the National Institutes of Health, and grant numbers PR033005 and DAMD17-02-1-0211 from the Department of Defense. Accordingly, the United States government may have certain rights in the invention.

FIELD

The present application relates to the development and use of attenuated strains of malarial parasites as vaccines for the prevention and treatment of malaria.

BACKGROUND

A global public health goal is the control and eventual eradication of human malaria, which is caused primarily by one of four species of the *Plasmodium* parasite: *P. falciparum, P. vivax, P. malariae*, and *P. ovale*. It is estimated that over 500 million people in tropical regions are exposed to malaria annually, and 1.5 to 2 million people die from this disease. Efforts to control malaria have historically focused on control of the mosquito vector and the development of anti-malarial drugs. These efforts have met with only limited success. New prophylactic and therapeutic drugs are of limited effectiveness because drug-resistant strains can appear rapidly in endemic areas. Control of the mosquito vector depends largely upon implementation of insecticide-based control programs which, due to cost and other factors, are difficult to maintain in developing nations. Vector resistance to modern insecticides has compounded the problem, and resulted once again in the resurgence of malaria.

Mammalian hosts can be infected by the sporozoite form of the malaria parasite, which is injected by the female *Anopheles* mosquito during feeding. Sporozoites injected into the bloodstream are carried rapidly to the liver where they invade hepatocytes, the beginning of liver-stage infection. Once in hepatocytes, sporozoites develop into merozoite forms, which are released from hepatocytes and invade erythrocytes. Within the erythrocyte, the parasite asexually reproduces from rings to schizonts. This stage of the parasite's life cycle is known as the blood-stage. The mature schizont contains merozoites which, upon rupture of the erythrocyte, can invade other erythrocytes, causing clinical manifestations of the disease. Some merozoites differentiate into sexual forms, called gametocytes, which are taken up by mosquitoes during a blood meal. After fertilization of gametocytes in the mosquito midgut, developing ookinetes can penetrate the gut wall and encyst. Rupture of such oocysts allows release of sporozoites that migrate to the salivary glands to be injected when the female mosquito takes another blood meal, thus completing the infectious cycle. This stage, which occurs within the mosquito, is called the extrinsic cycle or mosquito stage.

Experiments conducted in the 1960s demonstrated that vaccination with X-irradiated sporozoites of *Plasmodium berghei* (*P. berghei*) protected mice against sporozoite challenge, which was lethal in unvaccinated animals. This observation was later extended to clinical studies in humans where immunization with X-irradiated sporozoites of *P. falciparum* or *P. vivax* protected human volunteers against sporozoite challenge delivered through the bites of infected mosquitoes. This protection was thought to be mediated by antibodies. Serum from immunized animals, including humans, formed a precipitate around the surface of live, mature sporozoites. This reaction has been termed the circumsporozoite precipitin (CSP) reaction. These same sera blocked the ability of sporozoites to invade human hepatoma cells in culture (ISI assay). In other studies, a single antigenic determinant localized on the surface of *P. berghei* sporozoites, termed the circumsporozoite protein, was identified. It was shown that a monoclonal antibody reacting with the circumsporozoite (CS) protein of *P. berghei* could passively transfer immunity to recipient animals. These animals were protected from sporozoite challenge in a dose-dependent fashion. Evidence also existed that cell-mediated immunity was important.

The first CS protein gene to be cloned was derived from the H strain of *P. knowlesi*, a simian parasite. The genes encoding the CS proteins of the human malaria parasites *P. falciparum, P. vivax*, the simian parasite *P. cynomolgi*, and the rodent parasite *P. berghei* were also cloned and sequenced. A characteristic feature of the CS genes of each of the parasites is a central region which encodes over one-third of the protein, containing a series of repeated peptide sequences. The primary amino acid sequence, the length of the repeated sequence, and the number of repeats vary with each species of parasite. The repeat region epitopes are characteristic of each species. The gene encoding the CS protein of *P. falciparum* specifies a central repeat region of a tetrapeptide (asn-ala-asn-pro) repeated 37 times, interrupted in four locations by the nonidentical tetrapeptide (asn-val-asp-pro). The central repeat region of *P. vivax* CS protein contains 19 nonapeptides; the central sequence of *P. knowlesi* contains 12 dodecapeptides, and the repeat region of *P. berghei* contains 12 octapeptides. Comparison of sequences from *P. knowlesi* (H strain) and *P. falciparum* and *P. vivax* reveals no sequence homology except for two short amino acid sequences flanking the repeat region, termed Region I and Region II.

Efforts to develop an effective anti-sporozoite vaccine for *P. falciparum* have used peptides derived from the circumsporozoite (CS) repeat region and the two flanking Region I and Region II sequences. These experiments showed that antibody to the repeat region but not to the conserved sequences recognized authentic CS protein, produced CSP activity, and blocked sporozoite invasion (ISI) in vitro. A recombinant DNA subunit vaccine composed of 32 *P. falciparum* tetrapeptide repeats fused to 32 amino acids of the tetracycline resistance gene was produced in *E. coli*. Likewise, a peptide-carrier vaccine composed of three repeats of the peptide asn-ala-asn-pro (NANP) conjugated to tetanus toxoid was developed. In each case, preclinical studies indicated that biologically active (as shown by CSP and ISI) anti-sporozoite antibodies were elicited as a result of immunization. Human safety and immunogenicity studies with both vaccines yielded similar results. Both vaccine preparations were well tolerated at doses ranging from 10 micrograms to 800 micrograms, and both elicited some anti-CS antibodies in all immunized subjects. However, high titers were not achieved. In addition, subsequent booster immunizations with the peptide-carrier vaccine did not result in increased antibody titers. Several individuals from each study were then challenged with live sporozoites in order to test the efficacy of these vaccine preparations. Once again, similar results were achieved with both vaccines; the level of protection (as measured by a delay in the appearance of blood stage parasites) correlated with the anti-CS antibody titers of the challenged individuals, but in each trial, only one individual was protected. Parallel studies to evaluate the feasibility of human subunit vaccine development have been examined in the rodent *P. berghei* malaria model.

Another study has reported that levels of naturally acquired antibodies to the *P. falciparum* CS protein, as high as those achieved by a subunit sporozoite vaccine, did not protect against *P. falciparum* infection during a 98-day interval in a malaria-endemic area.

In different studies, subunit vaccines containing peptides of other *P. falciparum* antigens have been investigated. In addition, recombinant vaccinia viruses, which express *P. falciparum* antigens, have been described for use. More current approaches to malaria vaccines also include DNA vaccines, a malaria specific protein developed using transgenic technology as a vaccine, as well as genomic and proteomic approaches.

Perspectives and advances in malaria vaccination have been described (Miller, L. H., et al., 1984, *Phil. Trans. R. Soc. Lond.* B307:99-115; 1985, VACCINES 87, Channock et al., eds., Cold Spring Harbor Laboratory, Cold Spring Harbor, N.Y. pp. 81-106, 117-124). More recent advances in malaria vaccines are described in a review paper entitled "Malaria Vaccine Development: Status Report" (S. James and L. Miller, Institute of Allergy and Infectious Diseases, NIH, Washington D.C.: GPO 2000), which can also be obtained on the website of the Division of Microbiology & Infectious Diseases, National Institute of Allergy and Infectious Disease, NIH.

There are many scientific questions that must be addressed in the course of further development efforts on malaria vaccines. These include issues such as how to induce appropriate (protective, long-lasting, nonpathogenic) immune responses, how to structure combination vaccines, how to deal with parasite antigen diversity and antigenic variation, as well as how to deal with human genetic restriction of immune response and/or genetic predilection toward detrimental responses.

There are also a number of hurdles related to research and evaluation of candidate vaccines. These include issues regarding the appropriateness and accessibility of animal models. Other technical hurdles relate to the need to identify assays for ongoing validation of candidate antigens through process development and scale-up production, as well as assays predictive of protection for assessment of immunogenicity and efficacy in clinical trials. In addition, much careful thought must be given to clinical trial design. This is especially true for blood-stage vaccines, where the feasibility of experimental challenge infection is extremely controversial and the optimal measurements of efficacy is reduced morbidity/mortality, as well as for sexual stage vaccines, where the ultimate measurement of efficacy is interruption of malaria transmission.

The development and widespread availability of highly effective attenuated malarial vaccines to provide efficacious immunization against malaria would be highly desirable and beneficial for humans at risk of contracting the disease. No approved malaria vaccine is currently available, and currently available drugs used to treat malaria are only partially effective.

SUMMARY

Vaccines and methods of inducing an immunogenic response to malaria are provided. The vaccines are targeted at the asexual (blood-stage) phase of the parasite's life, when the parasites are in red blood cells. The vaccines contain *Plasmodium* organisms lacking predetermined, essential metabolic functions.

The human malaria parasite *Plasmodium falciparum* relies on the acquisition of host purines for its survival within human erythrocytes. Purine salvage by the parasite requires specialized transporters at the parasite plasma membrane (PPM), but the exact mechanism of purine entry into the infected erythrocyte and the primary purine source utilized by the parasite remain unknown. As described herein, transgenic parasites lacking the PPM transporter PfNT1 are auxotrophic for hypoxanthine, inosine and adenosine under physiological conditions and are only viable if these normally essential nutrients are provided at excess concentrations. Transport measurement across the PPM and growth assays in media containing individual purines as sole purine sources in in demonstrated an essential role of PfNT1 in the transport of all naturally occurring purine nucleosides and nucleobases (El Bissati et al., *Proc. Nat. Acad. Sci. USA* (2006) 103:9286-9291; El Bissati et al., *Mol. Biochem. Parasitol.* (2008) 161: 130-129; Downie et al., *Euk. Cell* (2008) 7:1231-1237).

When injected into humans or primates, strains of *Plasmodium* lacking this essential nutrient transporter are expected to either stop growing or to undergo no more than two cycles of division due to the low availability of purines in plasma. Physiological concentrations of purines in plasma are in the range of about 0.5 µM to about 10 µM Therefore, these transgenic strains are useful as a safe and effective vaccine against malaria.

*Plasmodium falciparum* must also synthesize phosphatidylcholine (PtdCho) from host serine in order to build plasma membranes. The enzyme phosphoethanolamine methyltransferase (PfPMT) is essential for the synthesis reaction to occur. Applicants have discovered that nuclear division, cellularization and survival of the parasite within human erythrocytes is impacted when the expression of the PfPMT gene is disrupted. Disruption of the PfPMT gene results in complete loss of PtdCho biosynthesis from serine, major alterations in parasite cellularization and infectivity, reduced rate of survival of parasites, and severe disruption of sexual differentiation.

When injected into humans or primates, strains of *Plasmodium* with disrupted PfPMT function are expected to have a dramatically reduced rate of infectivity and survival, and possibly transmission. Therefore, these transgenic strains are useful as a safe and effective vaccine against malaria.

The malaria vaccines provided herein contain a transgenic malarial parasite in which at least one gene is modified and/or deleted such that the gene is non-functional, and in which the normally occurring gene encodes a protein necessary for continued in vivo survival, proliferation and infection of host red blood cells by the parasite. The species of malarial parasites to be included in the vaccines include, but are not limited to, *Plasmodium vivax, Plasmodium malaria, Plasmodium ovale* and *Plasmodium falciparum*. Exemplary strains of *P. falciparum* include the 3D7 strain, the Vietnam-Fort (FVO) strain, Uganda-Palo Alto (FUP) strain, FCH/4 (Philippines) strain, the falciparum Santa Lucia (Salvador I) strain and the Malayan Camp (MC) strain.

In one embodiment, the at least one gene of the malarial parasite that is rendered non-functional by modification or deletion normally encodes a protein necessary for nutrition of the malaria parasite, including a parasite plasma membrane transporter, such as an essential nutrient transporter (e.g., a purine transporter; a glucose transporter; an amino acid transporter, or a choline transporter).

In another embodiment, the at least one gene of the malarial parasite that is rendered non-functional by modification or deletion normally encodes a protein necessary for the formation of a component of the parasite plasma membrane, such as a phospholipid. Exemplary phospholipids include phosphatidylcholine (PtdCho) and phosphatidylethanolamine (ptdEtn), which compose 40-50% and 35-45%, respectively, of the malarial parasite's total plasma membrane phospholipid content.

The non-functional gene of the non-wild type malarial parasite in the vaccines is rendered non-functional by biological and chemical techniques well known to those skilled in the art such as mutation, attenuation, selection, knockout technology and/or homologous recombination.

In one embodiment the malaria vaccine contains a malarial parasite having two genes rendered non-functional, which, in their naturally occurring state, encode two proteins necessary for the continued in vivo survival, proliferation and infection of host red blood cells by the parasite.

A method is provided for producing a non-wild type malarial parasite having at least one non-functional gene by culturing the non-wild type malarial parasite at non-physiological concentrations of essential nutrients, such as purines or choline. Preferably the essential nutrients are those that are adversely utilized, processed or metabolized by the non-wild type malarial parasite and the non-physiological concentrations are higher than the concentrations of those nutrients in vivo. Optionally, malarial parasites are isolated from the medium containing non-physiological (higher than physiological) essential nutrient concentrations and are exposed for a length of time to much lower, physiological concentrations of essential nutrients. Such exposure may confer advantages to the effectiveness and/or reliability of the resulting malaria vaccine, for example, by conferring a greater degree of control and predictability on the number of cell divisions the attenuated parasite undergoes following administration of malarial vaccine to a human or animal subject.

In one embodiment, malarial parasites containing a non-functional gene for a purine transporter are cultured to grow and proliferate in vitro in purine concentrations in the range of at least about 50 μM to about 2 mM or, alternatively, in purine concentrations in the range of at least about 100 μM to about 1.5 mM.

In another embodiment, malarial parasites having a non-functional gene for an enzyme essential for the synthesis of PtdCho are cultured to grow and proliferate in vitro in choline concentrations in the range of at least about 50 μM to about 500 μM (e.g., but not limited to, about 50 to about 75 μM, about 50 to about 100 μM, about 50 to about 150 μM, about 50 to about 200 μM, about 50 to about 300 μM, about 50 to about 400 μM, about 50 to about 450 μM) and subranges thereof, or in choline concentrations in the range of at least about 200 μM to about 1 mM (e.g., but not limited to, about 200 to about 500 μM, about 500 to about 750 μM, about 750 to about 1000 μM), and subranges thereof.

Also provided herein are methods of eliciting an immune response in a host, comprising introducing into the host any one of the malaria vaccines mentioned above in an amount sufficient to elicit an immune response. In one embodiment the host is a human and the vaccine is administered by injection.

Also provided herein are methods of immunizing a host comprising introducing into the host any one of the malaria vaccines mentioned above in an amount sufficient to immunize the host against malaria. In one embodiment the host is a human and the vaccine is administered by injection.

Also provided herein are kits for immunizing an animal against malaria comprising a malarial parasite with at least one gene which has been rendered non-functional, wherein the non-functional gene, when present in naturally occurring form, encodes a protein necessary for continued in vivo survival, proliferation, and infection of host red blood cells by the parasite.

Further provided herein are methods for immunizing an animal against malaria comprising preparing a malarial parasite, wherein the malarial parasite comprises at least one gene rendered non-functional, wherein the non-functional gene, when present in naturally occurring form, encodes a protein necessary for continued in vivo survival, proliferation, and infection of host red blood cells by the parasite; growing and propagating the resulting attenuated malarial parasite using a growth medium comprising a higher than physiological concentration of one or more essential nutrients; isolating the attenuated parasite from the growth medium; and, administering the attenuated parasite in an amount sufficient to elicit an immune response in the animal.

In addition, also provided herein are live *Plasmodium* organisms that are genetically engineered to render a blood-stage-specific gene non-functional, wherein the non-functional gene, when present in naturally occurring form, encodes a protein necessary for continued in vivo survival, proliferation, and infection of host red blood cells by the parasite.

Also provided are methods for inoculating a vertebrate host against malaria, by administering to the host a live *Plasmodium* organism that is genetically engineered to render a blood-stage-specific gene non-functional.

Further provided are vaccine compositions comprising a live *Plasmodium* organism that is genetically engineered to render a blood-stage-specific gene non-functional.

Also provided are uses as a malaria vaccine of a live *Plasmodium* organism that is genetically engineered to render a blood-stage-specific gene non-functional.

Also provided are methods of producing a vaccine composition, by suspending in a pharmaceutically acceptable carrier solution a live *Plasmodium* organism that is genetically engineered to render a blood-stage-specific gene non-functional.

Other embodiments and advantages of the invention are set forth in part in the description which follows, and will be obvious from this description, or may be learned from the practice of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates the strategy for PfNT1 disruption by double cross-over; (A) Gene disruption strategy. I: schematic representation of wild-type PfNT1 chromosomal locus; II: the plasmid vector pKEΔPfNT1 used for stable transformation of *P. falciparum*; and III: the proposed model of integration of the plasmid by double cross-over into PfNT1 chromosomal locus. (B) Southern blot analysis of XbaI (X) and XbaI+HindIII (X-H) digested genomic DNA from wild-type (WT) and pfnt1Δ parasites using blasticidin-s-deaminase (BSD)-specific and PfNT1-specific probes (indicated by gray right-left arrows).

Figure 2:
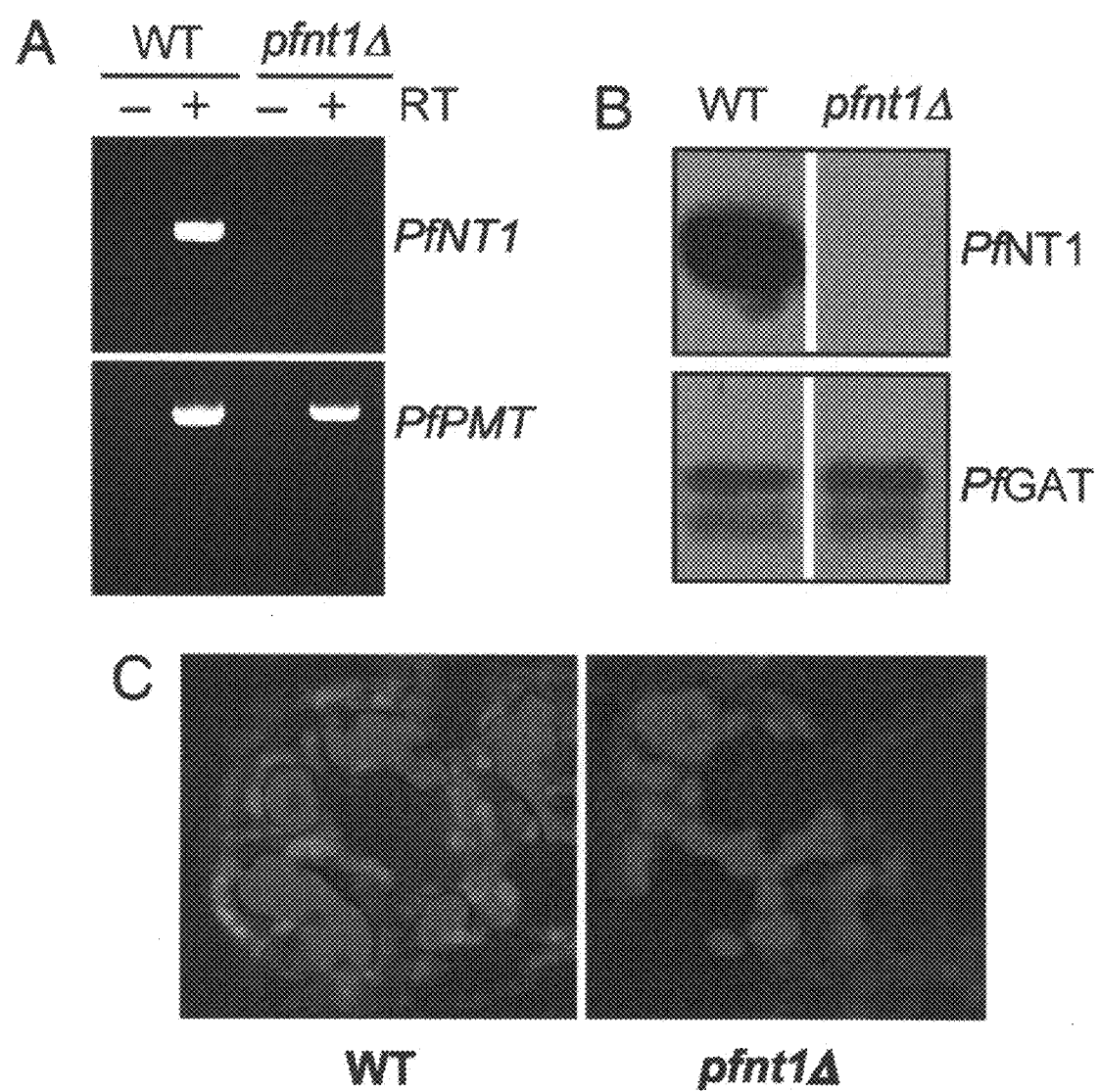

FIG. 2 illustrates the altered expression of PfNT1 in the pfnt1Δ strain; (A) RT-PCR analysis of RNA isolated from wild-type (WT) and pfnt1Δ strains using specific primers within the PfNT10RF. RT-PCR of the PfPMT cDNA is used as control. (B) Western blot analysis was performed using protein extracts from asynchronous cultures of wild-type and pfnt1Δ strains using PfNT1 antibodies; The glycerol-3-phosphate acyltransferase, PfGat, was used as an internal positive control. (C) Immunofluorescence microscopy of wild-type- and pfnt1Δ-infected RBCs at the schizont stage; DNA was counterstained with Hoechst dye (blue); In green, PfNT1 conjugated to the FITC-conjugated goat anti-rabbit secondary antibody; In red, Band 3 conjugated to Texas Red-conjugated anti-mouse secondary antibody.

Figure 3:
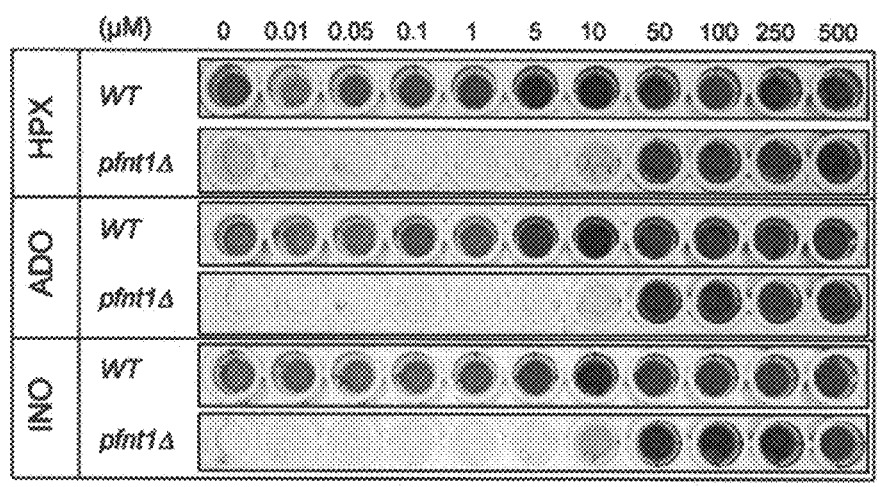
Figure 3:
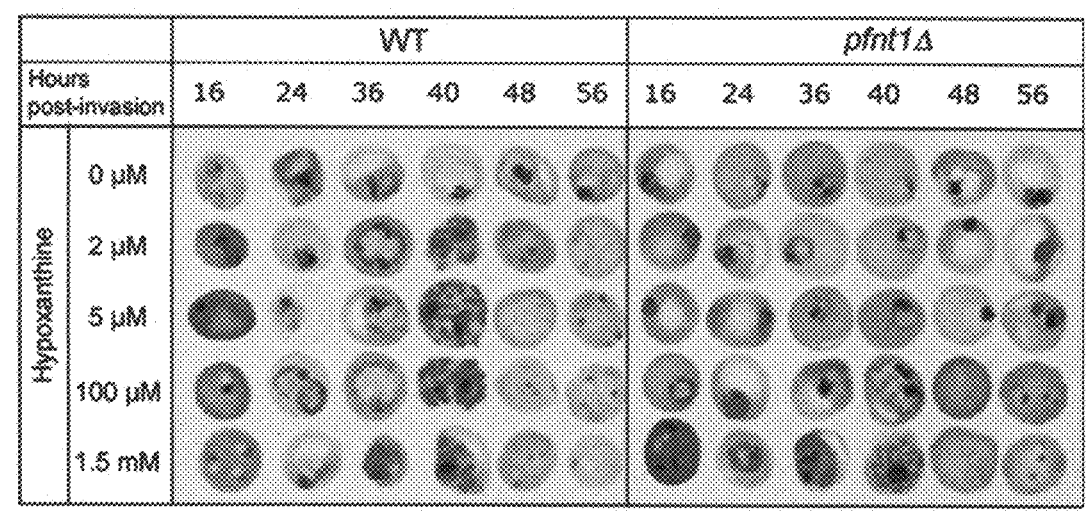

FIG. 3 illustrates the growth of pfnt1Δparasites in the presence of increasing concentrations of hypoxanthine (HPX), adenosine (ADO) or inosine (INO); (A) Parasite-specific lactate dehydrogenase assay, pLDH, to detect the growth of the parasites; (B) Synchronized WT and pfnt1Δ parasites grown at different concentrations of hypoxanthine (0, 2, 5, 100, and 1500 µM), were collected at different stages and analyzed by Giemsa stain, and evaluated by light microscopy.

Figure 4:
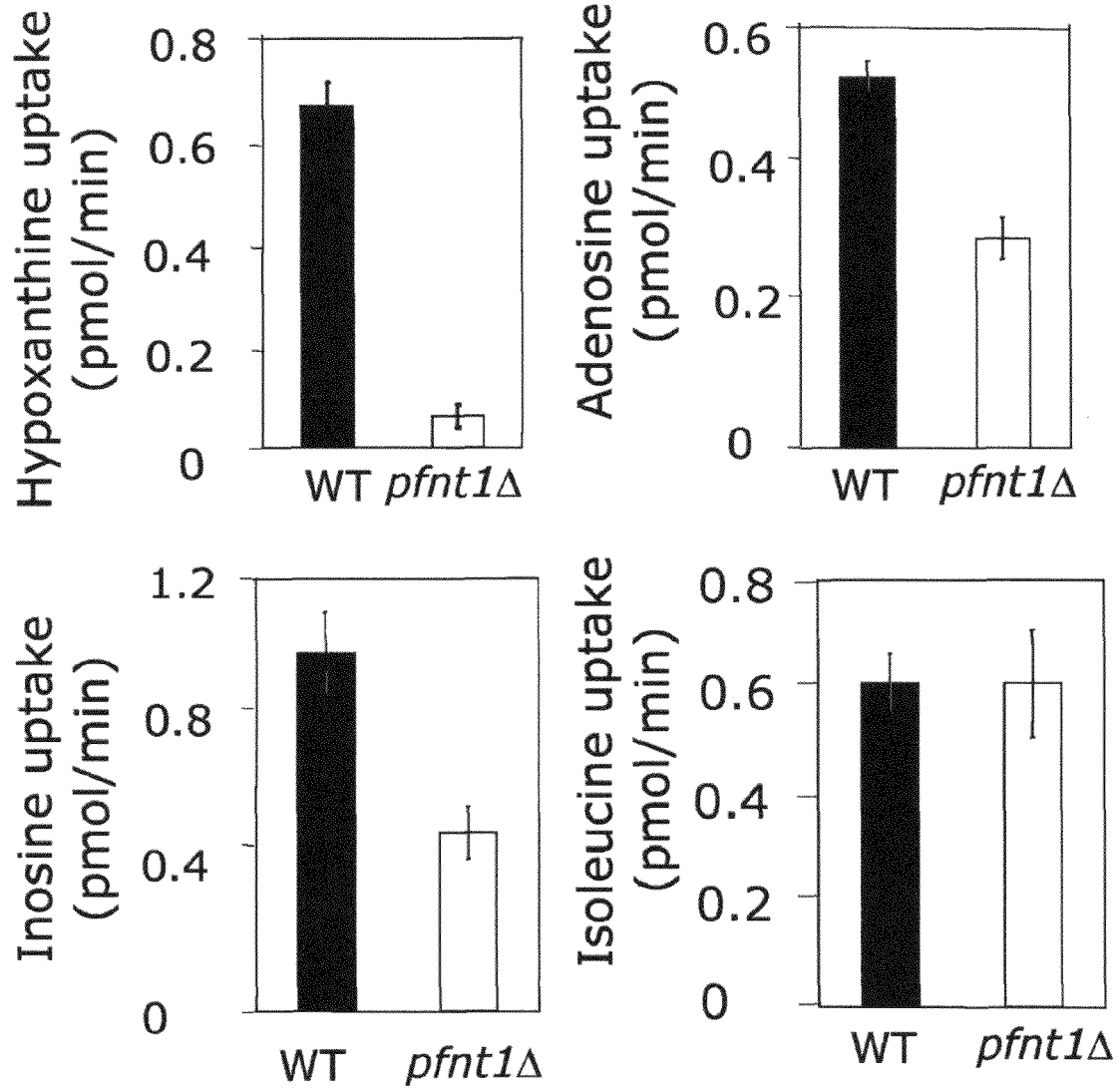

FIG. 4 illustrates purine uptake in wild-type (WT) and pfnt1Δ free parasites; Uptake of hypoxanthine, adenosine and inosine in free wild-type (WT) and pfnt1Δ trophozoites was performed as described in the Examples herein; isoleucine uptake is used as a control; These experiments were performed at least three times and each value is the mean±standard deviation of at least triplicate experiments.

Figure 5:
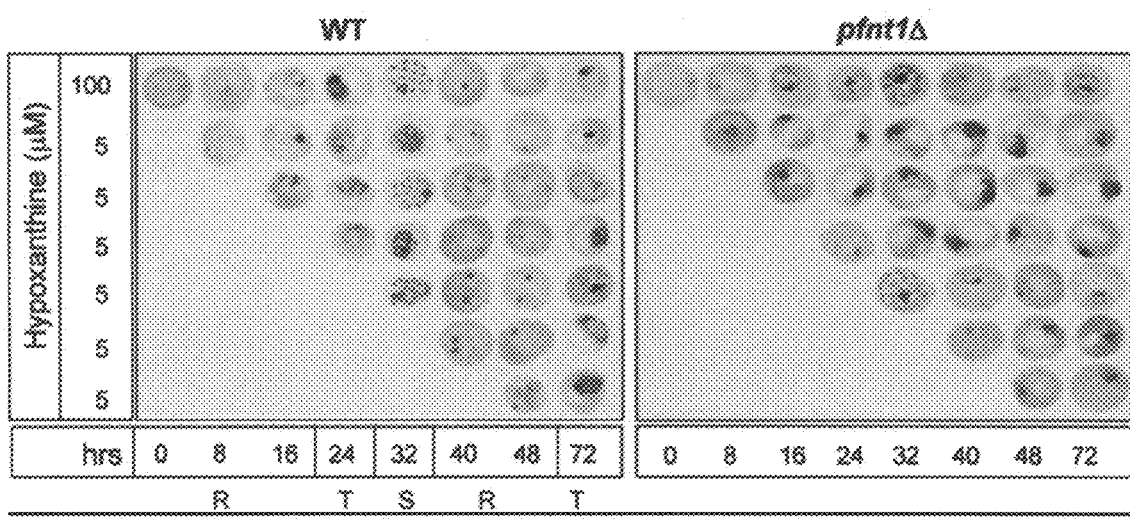

FIG. 5 illustrates that PfNT1 is required for parasite intraerythrocytic development but not essential for rupture of schizont-infected erythrocytes or invasion; Wild-type (WT) and pfnt1Δ strains were synchronized and at different stages (rings (R), trophozoite (T) and schizont (S)) transferred from medium containing 100 µM of hypoxanthine to medium containing 5 µM of this substrate; Parasite development was then monitored every eight hours post starvation by Giemsa staining and microscopy.

Figure 6:
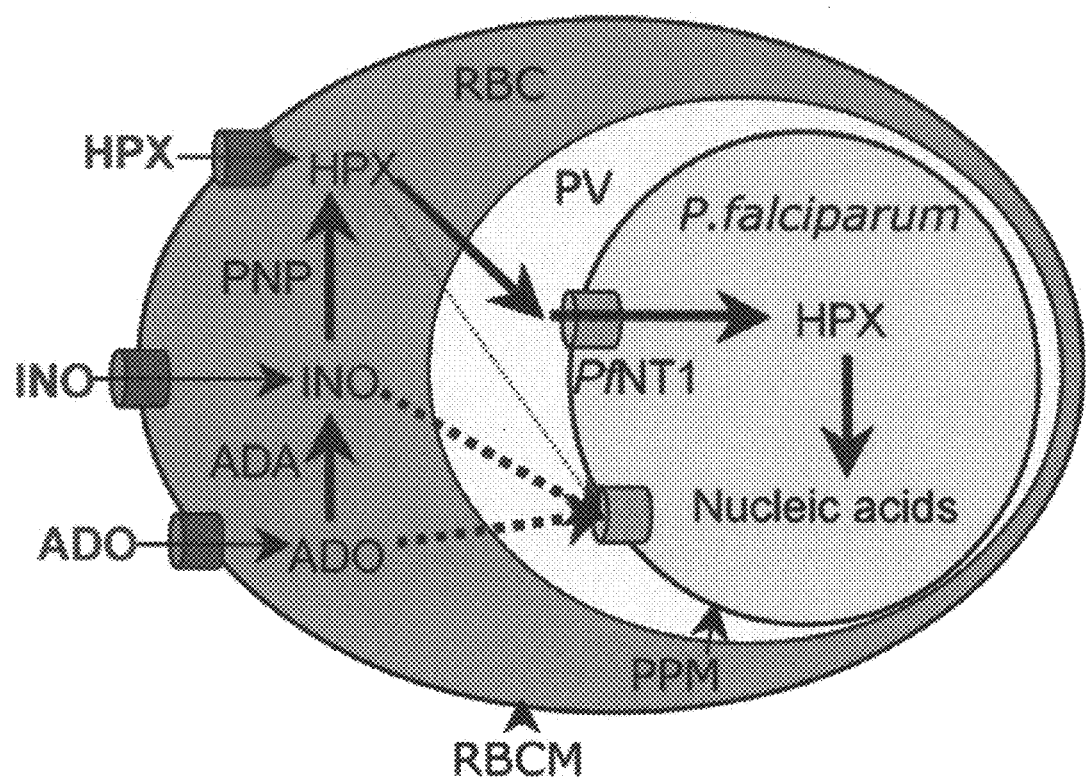

FIG. 6 illustrates a model for sequential purine uptake pathways in *P. falciparum*-infected erythrocytes; Hypoxanthine (HPX), adenosine (ADO) and inosine (INO) are transported into the red blood cell (RBC) cytoplasm via endogenous purine transporters. Inside the erythrocyte cytoplasm, adenosine and inosine are first converted into hypoxanthine before being transported along with transported hypoxanthine across the parasite plasma membrane (PPM) into the parasite cytoplasm; Alternative routes for entry of adenosine and inosine are represented in dotted lines. These additional transporters are unlikely to play an important role under physiological conditions. Guanine uptake into the parasite relies solely on PfNT1; PNP: purine nucleoside phosphorylase; ADA: adenosine deaminase; PV: parasitophorous vacuole; RBCM: red blood cell membrane.

Figure 7:
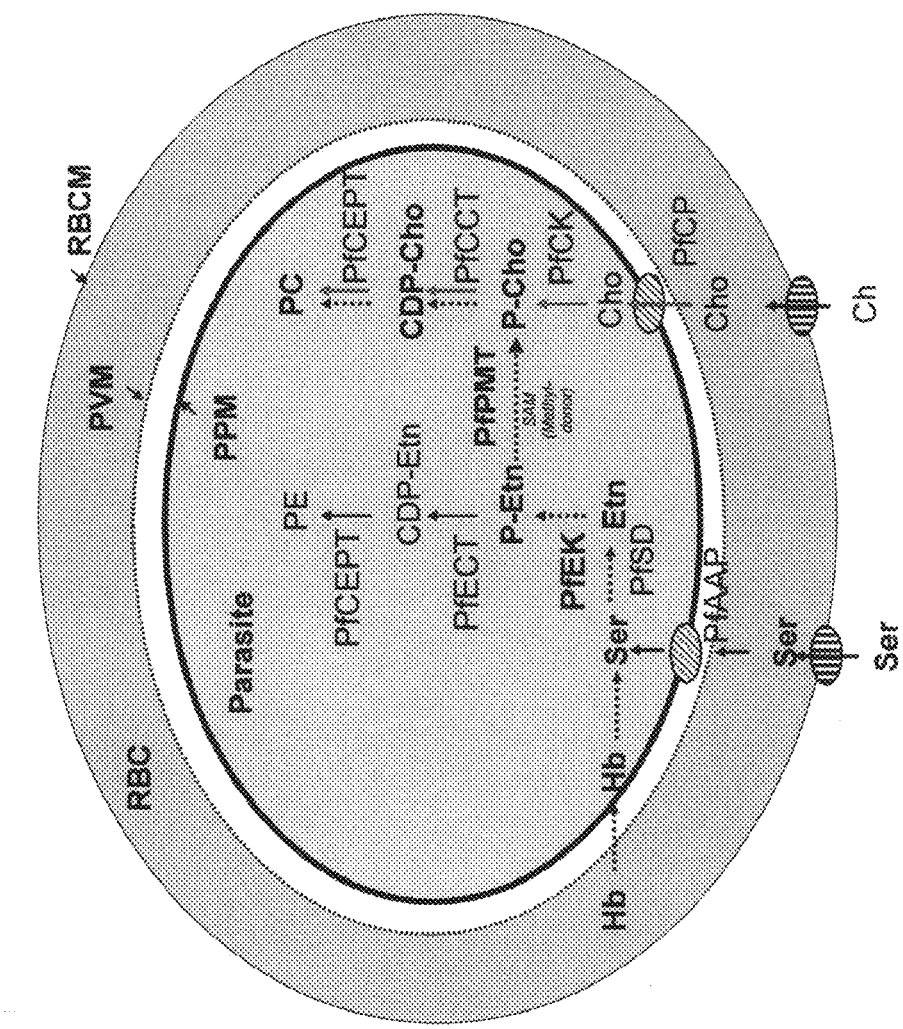

FIG. 7 illustrates pathways for the biosynthesis of phosphatidylcholine in *Plasmodium falciparum*. The CDP-choline pathway is shown with gray arrows. The SDPM pathway is depicted by dotted arrows. AAP, amino acid permease; Cho, choline; CDP, cytidine diphosphate; CDP-cho, CDP-choline; CDP-Etn, CDP-ethanolamine; HB, hemoglobin; PC, phosphatidylcholine; PE, phosphatidylethanolamine; PfCCT, *P. falciparum* CTP phosphocholine cytidylyltransferase; PfCEPT, *P. falciparum* choline/ethanolamine-phosphate transferase; PfCK, *P. falciparum* choline kinase; PfCP, *P. falciparum* choline permease; PfECT, *P. falciparum* CTP phosphoethanolamine cytidylyltransferase; PEEK, *P. falciparum* ethanolamine kinase; PfPMT, *P. falciparum* phosphoethanolamine methyltransferase; PPM, parasite plasma membrane; PVM, parasitophorous vacuolar membrane; RBC, red blood cell; RBCM, red blood cell membrane; SD, serine decarboxylase; Ser, serine.

Figure 8:
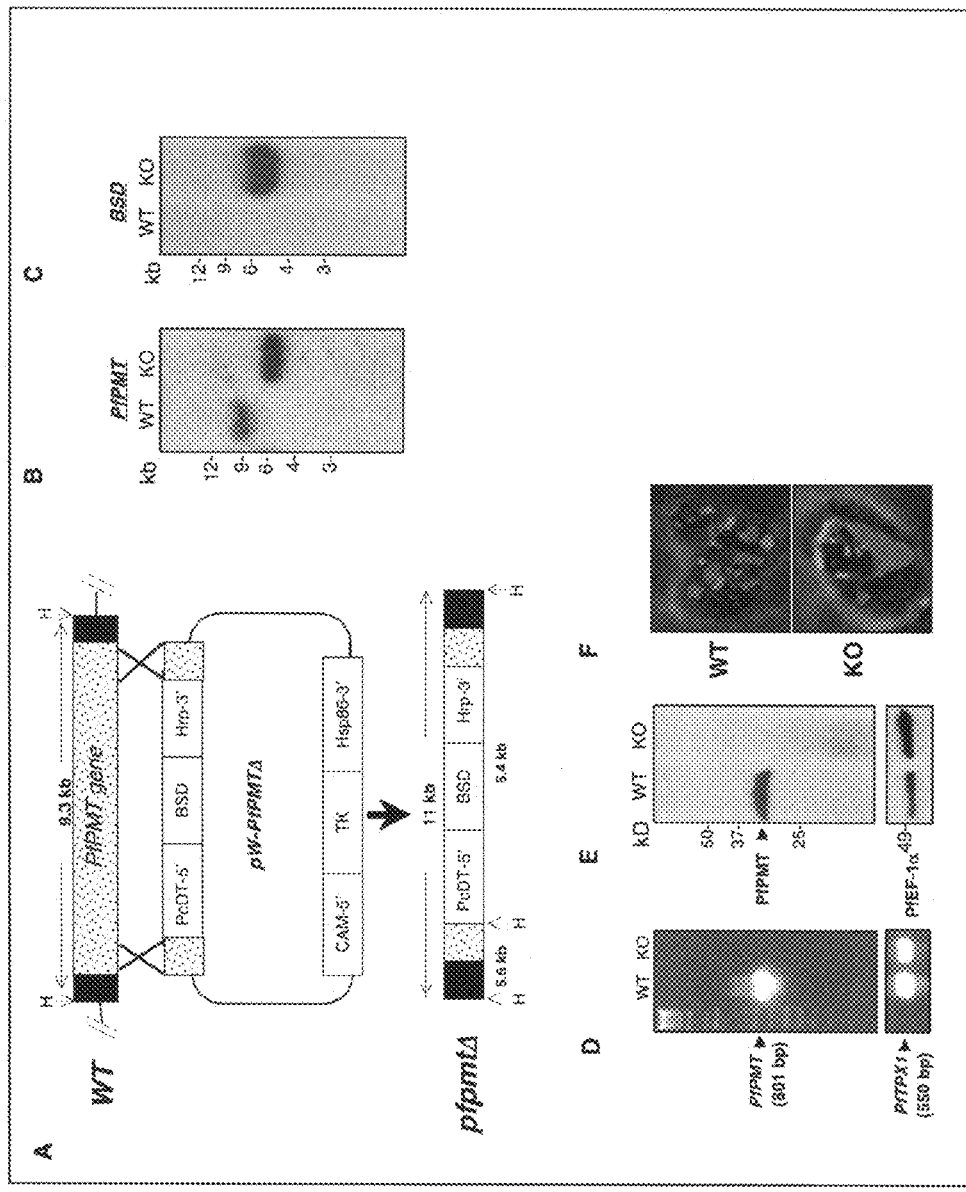

FIG. 8 illustrates the strategy for PfPMT gene disruption by double cross-over homologous recombination using a knockout plasmid construct pW-pfpmtΔ and characterization of the disruption of the PfPMT gene. (A) The wild type (WT) and the disrupted PfPMT gene (pfpmtΔ) loci are depicted with the HindIII (H) restriction sites used for Southern blot analysis. (B) Southern blot analysis of the HindIII-digested genomic DNA from the wild type (WT) and pfpmtΔ (knockout; KO) parasites using the PfPMT gene probe. (C) Using the blasticidin-s-deaminase (BSD) gene probe, a 5.4 kb fragment excised by HindIII digestion is recognized only in the KO and not in the WT parasites. (D) RT-PCR analysis of PfPMT gene transcription in WT and KO parasites. (E) Western blot analysis using protein extracts from asynchronous cultures of WT and KO parasites with anti-Pfpmt and anti-PfEF-1α (loading control) antibodies. (F) Immunofluorescence assay of WT and KO parasites using anti-PfPMT antibodies (green), Hoechst dye (blue) and anti-erythrocyte Band3 protein antibody (red).

Figure 9:
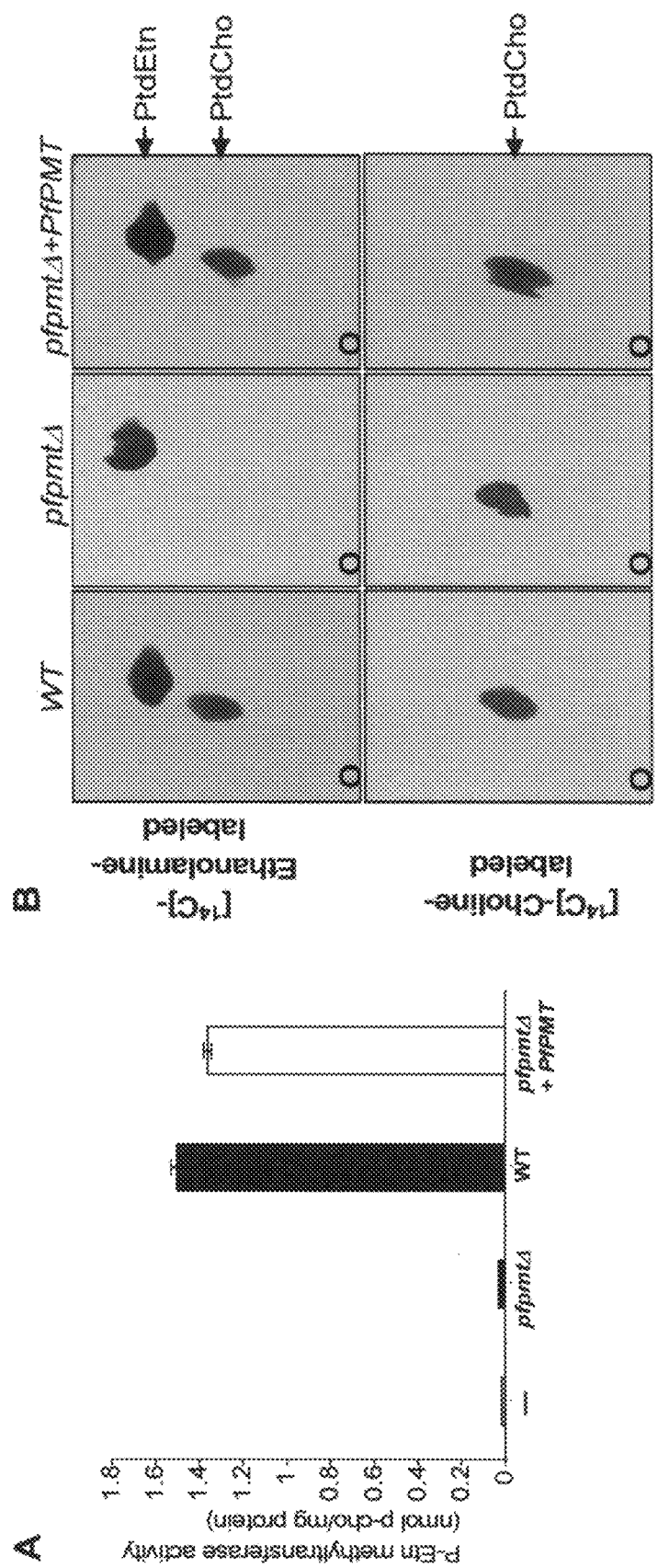

FIG. 9 illustrates the evidence for the loss of PfPMT enzymatic activity in the pfmptΔ strain compared to the wild type (WT) and pfpmtΔ+PfPMT strains. (A) PfPMT activity in *P. falciparum* extracts (50 µg total protein) was measured. The formation of radiolabeled phosphocholine was quantified by scintillation counting and the equivalent methyltransferase activity derived. Data are means±SD derived from triplicate experiments. (B) Synchronized wild type (WT), pfpmtΔ and pfpmtΔ+PfPMT parasites grown to 10% parasitaemia at early trophozoite stage in the absence of choline were labeled with either [14C]-ethanolamine (upper panels) or [14C]-choline (lower panels) and incubated for 12 h. The infected erythrocytes were washed twice in PBS and lipids extracted by the Folch method. The organic phase of the lipid extracts were resolved by 2-dimension thin-layer chromatography (TLC) and signals generated by autoradiography. O: sample application point; PtdEtn and PtdCho: positions of phosphatidylethanolamine and phosphatidylcholine, respectively.

Figure 10:
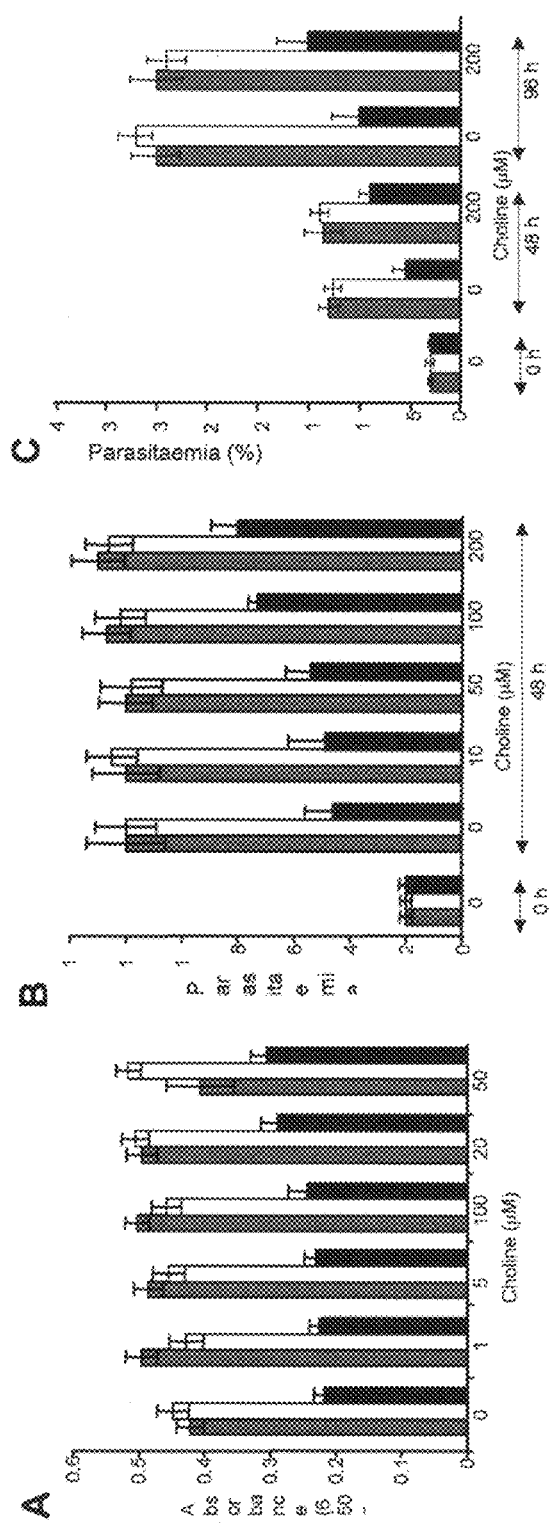

FIG. 10 is an illustration of parasite growth at different choline concentrations. (A) Parasite growth (with increasing choline concentration) represented by absorbance (650 nm) determined using the parasite lactate dehydrogenase assay at 48 h of culture. (B) Parasitemia determined by light microscopic counting of infected erythrocytes on Giemsa-stained thin smears of the parasite cultures at 0 h and 48 h of culture in medium with different concentrations of choline. (C) Parasitemia at 0, 48 and 96 h of culture in medium with 0 or 200 µM of choline. Gray, white and black columns represent absorbances for the wild type, the pfpmtΔ+PfPMT and pfpmtΔ parasite strains, respectively. Data are means±SD of triplicate assays.

Figure 11:
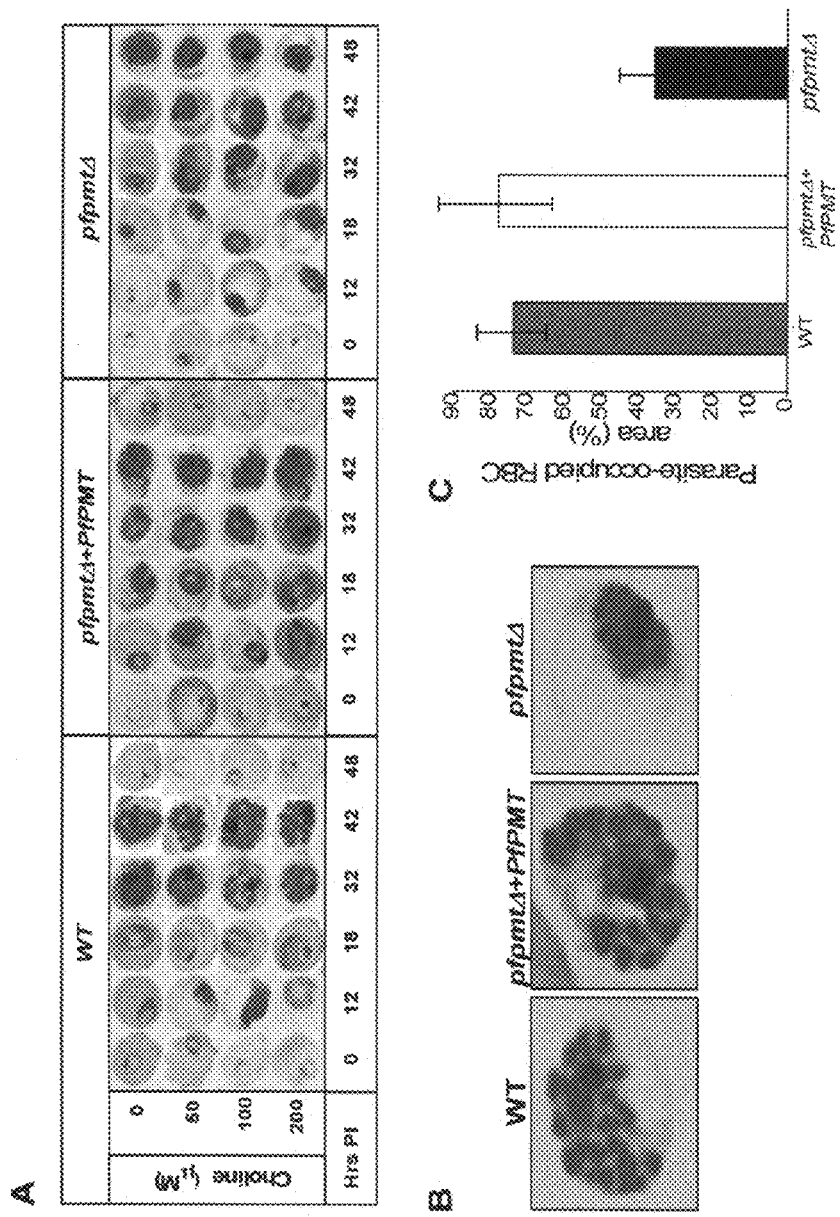

FIG. 11 is an illustration showing the progression of different parasite strains, grown at different concentrations of choline. (A) Progression of synchronized wild type, pfpmtΔ+PfPMT and pfpmtΔ parasite strains, grown at different concentrations of choline. The Giemsa-stained smears were prepared at different time points of culture (hours post-invasion) as indicated and examined by light microscopy. (B) Representative images of schizonts for the wild type (WT), pfpmtΔ+PfPMT and pfpmtΔ parasites. (C) Comparison of the RBC area (%) occupied by a mature schizont stage of the WT, pfpmtΔ+PfPMT and pfpmtΔ (gray, white and black columns, respectively). Values are means of ten different schizont-infected RBCs examined for each parasite strain with standard deviations of the means shown as error bars.

Figure 12:
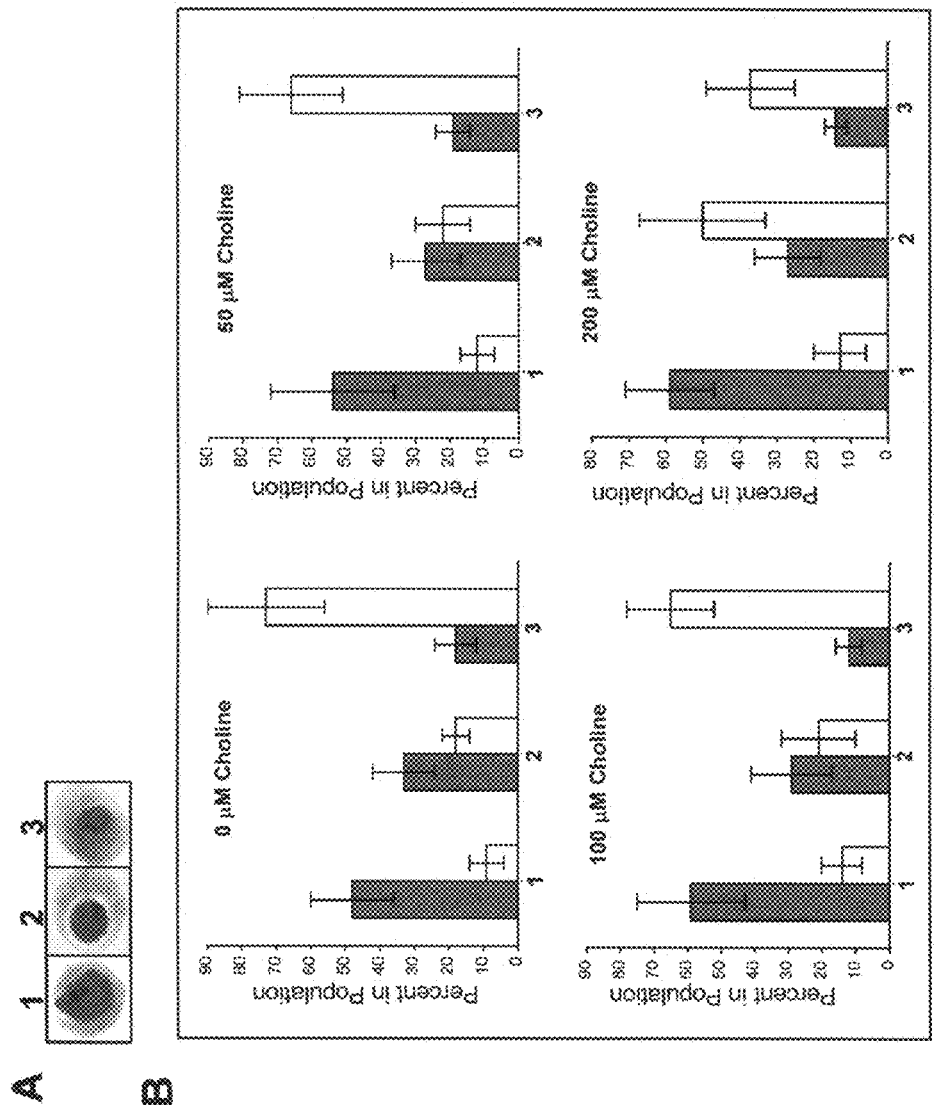

FIG. 12 is an illustration of the mean percentage in population of different forms of trophozoites at 32 h after invasion of erythrocytes. (A) Depicted are the three different forms of trophozoites, 1, 2 and 3, observed on Giemsa-stained smears of the wild type and pfpmtΔ parasites in cultures. The parasite occupies 60%, 40% and 20% of the RBC area in the forms 1, 2 and 3, respectively. (B) Shown is the percent population of the forms 1, 2 and 3 of trophozoites in the wild type (gray columns) and pfpmtΔ parasites (white columns) cultured with 0, 50, 100, and 200 μM choline in the medium. Values are means±SD of three independent cell counts of 200 infected cells per count.

Figure 13:
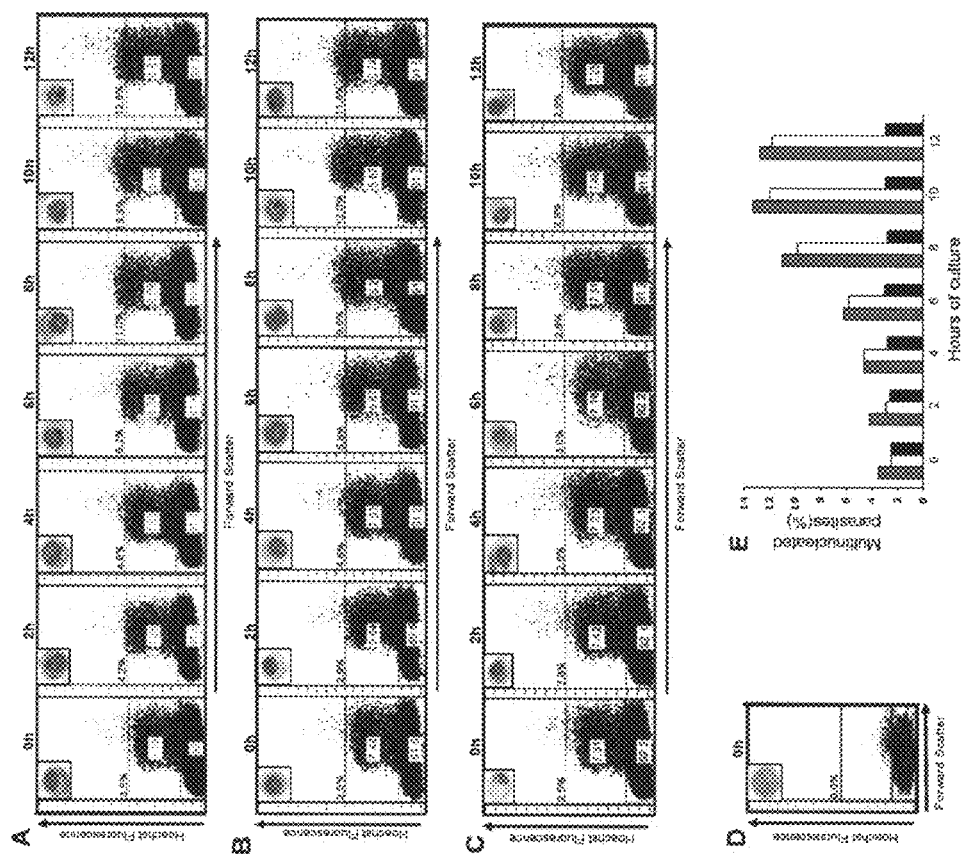

FIG. 13 is an illustration of flow cytometric analysis of parasites' progression from trophozoite to schizont stage by measuring Hoechst fluorescence intensity (relative nuclear DNA content). Profiles for the uninfected red blood cells, wild type, pfpmtΔ, and pfpmtΔ+PfPMT parasites are depicted in panels A, B, C and D, respectively, at 0 h and 12 h of culture. Numeric insets in the lower and mid portions of the panels represent the relative proportions of the 1 million cells sorted per sample, while the percent inset in the upper portion of the panels represent the proportion of multinucleated cells (schizonts) relative to cells with a single nucleus (trophozoites). Representative microscopic images of the Giemsa-stained smears of the parasitized cells sampled at each time point are shown as insets. (E) Proportion of multi-nucleated cells (schizonts) relative to cells with a single nucleus (trophozoites) at different time points of culture for the wild type (gray), pfpmtΔ+PfPMT (white), and pfpmtΔ (black) are represented in graphic format.

Figure 14:
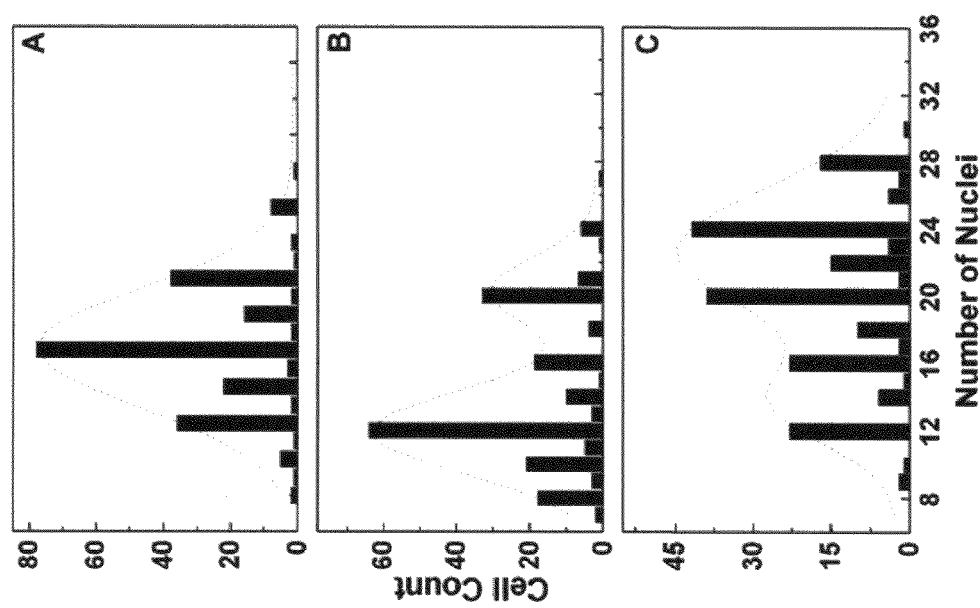

FIG. 14 is an illustration of the determination of nuclei counts for live parasitized red blood cells (RBCs) by Spinning Disc Confocal Microscopy. Panel A represents a population of 220 RBCs infected with pfpmtΔ+PfPMT parasites. Panel B represents a population of 198 RBCs infected with pfpmtΔ parasites cultured in medium without choline. Panel C represents a population of 194 RBCs infected with pfpmtΔparasites cultured in medium containing 21 μM of choline.

Figure 15:
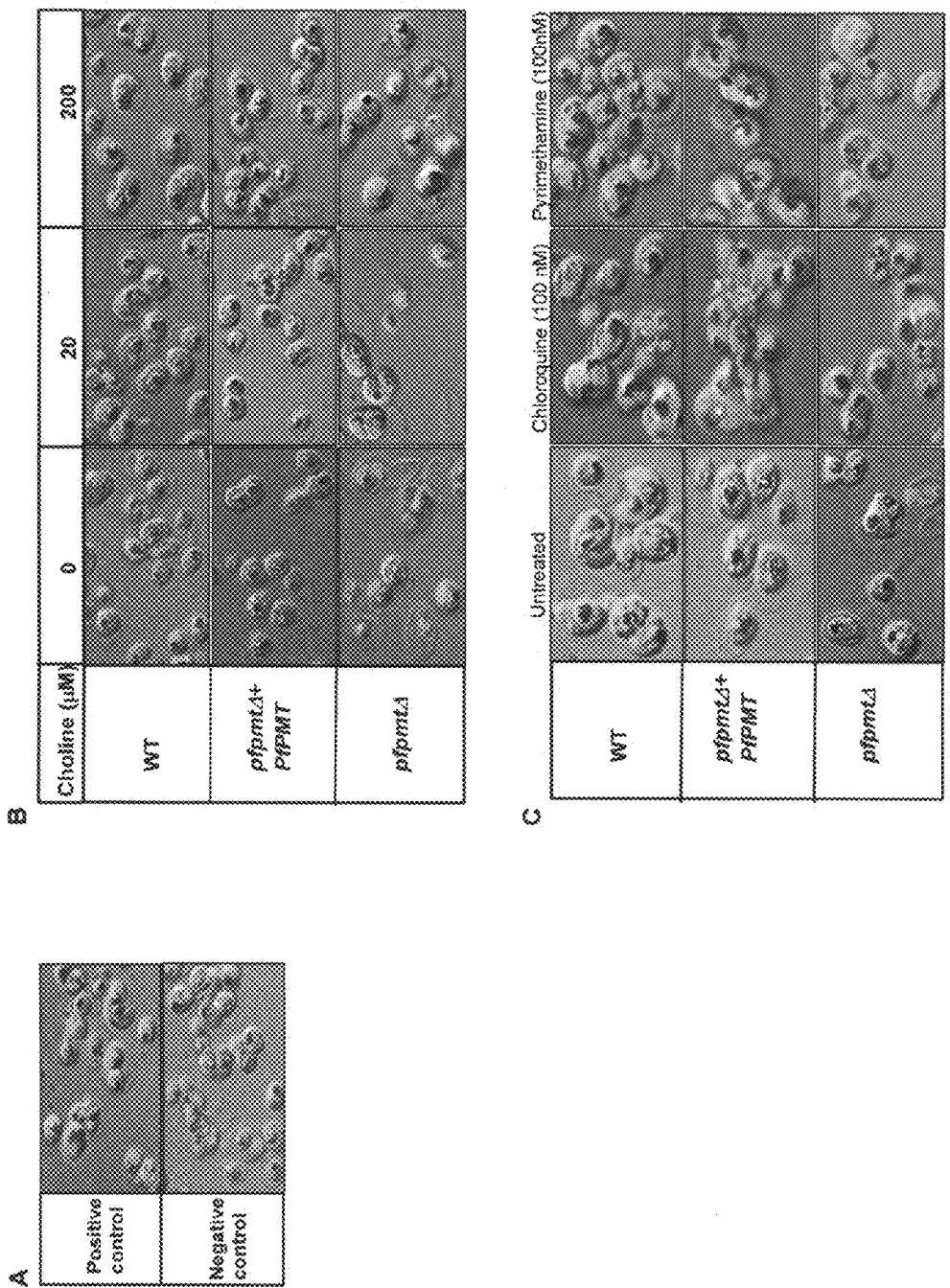

FIG. 15 is a depiction of the results from a TUNEL assay to determine parasite viability by detection of parasite DNA fragmentation. (A) Positive (green fluorescence) and negative (no fluorescence) control TUNEL assays for the wild-type parasites. (B) Wild type (WT), pfpmtΔ+PfPMT, and pfpmtΔ parasites cultured in medium with different concentrations (0, 20, and 200 μM) of choline and tested for apoptosis by the TUNEL assay. (C) WT, pfpmtΔ+PfPMT and pfpmtΔ parasites were cultured in the presence of either 100 nM pyrimethamine or 100 nM chloroquine for 24 hours and tested for apoptosis by the TUNEL assay.

DETAILED DESCRIPTION

Vaccines and methods of immunization targeted at the asexual (blood) phase of the malarial parasite's life, when the parasites are in red blood cells, are provided herein. Attenuated strains of malaria parasites are cultured and propagated in vitro under controlled conditions that require higher than physiological concentrations of one or more nutrients that are essential for the parasite. These attenuated strains have little if any ability to grow under in vivo conditions, such as following an injection for the purposes of vaccination.

Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials; methods, and examples are illustrative only and are not intended to be limiting.

Reference is made to standard textbooks of molecular biology that contain definitions and methods and means for carrying out basic techniques, encompassed by the present invention. See, for example, SAMBROOK ET AL., MOLECULAR CLONING: A LABORATORY MANUAL, Third Edition, Cold Spring Harbor Laboratory Press, New York (2001); CURRENT PROTOCOLS IN MOLECULAR BIOLOGY, Ausubel et al (eds.), John Wiley & Sons, New York (2001) and the various references cited therein.

Nutrient Requirements of Malarial Parasites

As mentioned above, malaria is one of the foremost threats to human health in the tropical regions of the world (*World Health Organ Tech Rep Ser* (2000) 892, i-v, 1-74). The disease is especially challenging to treat because of the widespread emergence of drug-resistant parasites and the limited number of available antimalarial drugs. As a consequence, better antimalarial therapies are urgently needed. *Plasmodium falciparum*, the causative agent of the most deadly form of human malaria, exhibits a complex life cycle that involves both an invertebrate vector, the *Anopheles* mosquito, and humans. While the ability of the parasite to invade human red blood cells (RBCs) provides it with an ideal refuge from immune attacks during the blood-stage of infection, RBCs are deficient in various nutrients required for parasite survival and multiplication. Therefore, the parasite has evolved novel transport machineries and specialized enzymes to acquire and metabolize host nutrients. Perhaps most striking is the nutritional requirement for purines. Unlike mammalian cells which synthesize purines de novo, *P. falciparum* is incapable of purine biosynthesis and has consequently evolved a unique complement of purine salvage enzymes that enables the parasite to scavenge host purines (Gero, A. M. & O'Sullivan, W. J. (1990) *Blood Cells* 16, 467-84; discussion 485-98; Sherman, I. (1998) in *Malaria: Parasite Biology, Biogenesis, Protection*, ed. Sherman, I., Ed (American Association of Microbiology Press, pp. 177-184; and Sherman, I. W. (1979) *Microbiol Rev* 43, 453-95). The first step of purine acquisition entails the uptake of purines from the host milieu. Because of the essential function of purine salvage in parasite growth and multiplication, purine transporters are regarded as ideal targets for the development of novel therapeutic strategies to combat malaria (Gero, A. M. & Upston, J. M. (1994) *Adv Exp Med Biol* 370, 493-8).

While it is known that purine transport across the PPM requires specialized purine transporters (Upston, J. M. & Gero, A. M. (1995) *Biochim Biophys Acta* 1236, 249-58), the pathways of purine translocation between the intracellular parasite and the host environment are unknown. Uninfected RBCs express a high affinity, equilibrative nucleoside transporter, hENT1, that mediates the sodium-independent uptake of a broad spectrum of purine and pyrimidine nucleosides (Boleti, H., Coe, I. R., Baldwin, S. A., Young, J. D. & Cass, C. E. (1997) *Neuropharmacology* 36, 1167-79). RBCs also harbor adenosine deaminase (ADA) and purine nucleoside phosphorylase (PNP) enzymes, which convert adenosine and inosine into hypoxanthine. However, the role of host transporters and enzymes in purine salvage by the parasite remains unknown. Furthermore, it is not known whether intraerythrocytic *P. falciparum* salvage a full complement of purine nucleosides and nucleobases from the RBC cytosol or solely hypoxanthine. Recently, PfNT1 was the first purine transporter to be identified and functionally characterized at the molecular level in *Plasmodium* (Carter, N. S., Ben Mamoun, C., Liu, W., Silva, E. O., Landfear, S. M., Goldberg, D. E. & Ullman, B. (2000) *J Biol Chem* 275, 10683-91; Rager, N., Mamoun, C. B., Carter, N. S., Goldberg, D. E. & Ullman, B. (2001) *J Biol Chem* 276, 41095-9; and Parker, M. D., Hyde, R. J., Yao, S. Y., McRobert, L., Cass, C. E., Young, J. D., McConkey, G. A. & Baldwin, S. A. (2000) *Biochem J* 349, 67-75). PfNT1 shares sequence and topological similarities to well-characterized transporters of the eukaryotic equilibrative nucleoside transporter family. However, the primary sequence of PfNT1, its substrate specificity, kinetic properties and inhibition profile are sufficiently different from hENT1, to suggest that if PfNT1 plays an essential function in *P. falciparum* development and multiplication it could be an excellent drug target.

Expression studies in *Xenopus laevis* oocytes revealed that PfNT1 has a broad ligand specificity for D- and L-nucleosides as well as for nucleobases (Carter, N. S., Ben Mamoun, C., Liu, W., Silva, E. O., Landfear, S. M., Goldberg, D. E. & Ullman, B. (2000) *J Biol Chem* 275, 10683-91; Rager, N., Mamoun, C. B., Carter, N. S., Goldberg, D. E. & Ullman, B. (2001) *J Biol Chem* 276, 41095-9; and Parker, M. D., Hyde, R. J., Yao, S. Y., McRobert, L., Cass, C. E., Young, J. D., McConkey, G. A. & Baldwin, S. A. (2000) *Biochem J* 349, 67-75), such as purines and pyrimidines. In this heterologous transport system, Carter and colleagues showed that PfNT1 has a high affinity for adenosine (Carter, N. S., Ben Mamoun, C., Liu, W., Silva, E. O., Landfear, S. M., Goldberg, D. E. & Ullman, B. (2000) *J Biol Chem* 275, 10683-91) and provided indirect evidence that hypoxanthine was not a high affinity ligand (unpublished data), whereas Parker and colleagues found that PfNT1 has a low affinity for both adenosine and hypoxanthine (Parker, M. D., Hyde, R. J., Yao, S. Y., McRobert, L., Cass, C. E., Young, J. D., McConkey, G. A. & Baldwin, S. A. (2000) *Biochem J* 349, 67-75). Subsequent studies with infected-RBCs revealed that PfNT1 is localized to the parasite plasma membrane (PPM) and expressed throughout the intraerythrocytic life cycle but is maximally expressed prior to parasite schizogony at the peak of nucleic acid utilization (Rager, N., Mamoun, C. B., Carter, N. S., Goldberg, D. E. & Ullman, B. (2001) *J Biol Chem*, 276, 41095-9). Since the initial characterization of PfNT1, three other putative equilibrative nucleoside transporters, designated PfNT2, PfNT3 and PfNT4, have been identified within the *P. falciparum* genome. However, as yet these have not been functionally authenticated and thus, their contribution to parasite purine acquisition remains undetermined.

As described herein, the ability to create a conditionally lethal pfnt1Δ mutant in *P. falciparum* establishes that PfNT1 is absolutely required for purine acquisition by *P. falciparum* under physiological circumstances. *P. falciparum* cannot synthesize purine nucleotides de novo and obligatorily depend upon purine salvage from the host for their synthesis of nucleotides and nucleic acids, and consequently for their ability to proliferate and cause disease. The loss of PfNT1 activity results in inhibition of parasite growth under physiological conditions under which concentrations of salvageable purines have been reported to be between 0.4-6 μM (Traut, T. W. (1994) *Mol Cell Biochem*, 140, 1-22). This growth defect can be suppressed by the addition of excessive, non-physiological levels of hypoxanthine, adenosine, or inosine, thus enabling purine acquisition by some additional but unknown mechanism and pharmacologically circumventing the genetic consequences of the conditionally lethal mutation.

The Role of PfNT1 in Hypoxanthine Uptake Across the PPM

Purine transporters have been identified in several parasitic protozoa and their biochemical properties and sensitivities to inhibitors have been determined in a number of heterologous expression systems within null backgrounds (Carter, N. S., Landfear, S. M. & Ullman, B. (2001) *Trends Parasitol*, 17, 142-5). Using a parallel approach, PfNT1 was shown to have a relatively high affinity for adenosine and a lower affinity for inosine and hypoxanthine (Carter, N. S., Ben Mamoun, C., Liu, W., Silva, E. O., Landfear, S. M., Goldberg, D. E. & Ullman, B. (2000) *J Biol Chem*, 275, 10683-91; Parker, M. D., Hyde, R. J., Yao, S. Y., McRobert, L., Cass, C. E., Young, J. D., McConkey, G. A. & Baldwin, S. A. (2000) *Biochem J*, 349, 67-75). Interestingly, pfnt1Δ parasites were non-viable at physiological concentrations of hypoxanthine, adenosine or inosine and exhibited relatively normal intraerythrocytic cycle only at higher concentrations of these substrates. These results demonstrated that under physiological conditions, PfNT1 is essential for hypoxanthine, adenosine and inosine uptake into the parasite, and that at higher concentrations these substrates could be transported via a secondary mechanism. The ability of RBC-liberated pfnt1Δ parasites to effectively transport adenosine and inosine demonstrates that the PPM harbors one or more additional permeases capable of transporting these nucleosides. Because nutrient limitation studies verified that adenosine and inosine do not support growth of the pfnt1Δ mutant at physiological concentrations, these data imply that these nucleosides do not reach the PPM membrane in their native form. Rather, adenosine and inosine are converted in the RBC cytoplasm into a PfNT1 substrate (FIG. 6). Hypoxanthine is the most likely candidate for this substrate, since RBCs are known to express high levels of both adenosine deaminase and purine nucleoside phosphorylase activities (Daddona, P. E. & Kelley, W. N. (1977) *J Biol Chem*, 252, 110-5; Lewis, A. S. & Lowy, B. A. (1979) *J Biol Chem*, 254, 9927-32), which sequentially metabolize adenosine to inosine and then to hypoxanthine. This hypothesis is supported by the fact that *P. falciparum*-infected RBCs are capable of converting radiolabeled adenosine into hypoxanthine in the RBC cytoplasm and subsequently, radiolabeled hypoxanthine could be detected in the parasite cytoplasm (Yamada, K. A. & Sherman, I. W. (1981) *Mol Biochem Parasitol*, 2, 349-58; Sherman, I. (1998) *Malaria, Parasite Biology, pathogenesis and Protection* (ASM Press, Washington D.C.)).

Nutrient Uptake into *P. falciparum* is Sequential

In the past 30 years, three models have been proposed to account for the movement of nutrients between the host and the intracellular parasite (Kirk, K. (2001) *Physiol Rev*, 81, 495-537). In the first model, referred to as the "sequential pathway," nutrients are first transported across the RBC membrane into the erythrocyte cytoplasm, and then translocated into the parasite after crossing the parasitophorous vacuolar membrane (PVM) and the PPM using specialized PPM transporters. In the second model, referred to as the "endocytosis model", nutrients are first transported across the RBC membrane into the erythrocyte cytoplasm and then progress into the parasite by endocytosis. The third model involves specialized entry mechanisms, referred to as the "parallel pathways," that allow direct movement of nutrients between the host medium and the parasite without entering the erythrocyte cytoplasm. These results strongly support a sequential pathway mechanism for entry of exogenous purines into *P. falciparum* (FIG. 6), because the parasite harbors additional pathways capable of transporting adenosine and inosine, although at physiological concentrations these purines are not capable of supporting the growth of knockout parasites. This supports the conjecture that these nucleosides do not gain direct access to the parasite and that they require prior conversion into hypoxanthine, reactions that occur within the RBC cytoplasm.

The Role of Other Permeases in Malarial Purine Uptake

Growth of pfnt1Δ could be maintained only at high concentrations of hypoxanthine, adenosine or inosine. Furthermore, transport studies in free-parasites revealed that the PPM harbors additional mechanisms capable of transporting adenosine or inosine. The completed genome sequence of *P. falciparum* revealed three nucleoside permease candidates, all members of the equilibrative nucleoside transporter family, for purine permeases (Martin, R. E., Henry, R. I., Abbey, J. L., Clements, J. D. & Kirk, K. (2005) *Genome Biol*, 6, R26). Whether these putative permeases are capable of recognizing and transporting nucleosides and whether they are expressed at the PPM await further investigation. The results, however, suggest that additional PPM permeases are unlikely to play an important role in parasite intraerythrocytic development, that PfNT1 is the major route of purine uptake under physiological conditions, and that PfNT1 is essential for intraerythrocytic parasite development.

The conditional lethality of the pfnt1Δ mutation in *P. falciparum* establishes that PfNT1 is absolutely indispensable for purine acquisition by *P. falciparum* under physiological purine conditions and that PfNT1 is the major route for purine salvage. This study also substantiates that erythrocyte enzymes convert exogenous adenosine and inosine to hypoxanthine prior to translocation into the parasite by PfNT1. Although PfNT1 shares sequence and topological similarities with hENT1 (human equilibrative nucleoside transporter 1) the major nucleoside transporter in human cells including erythrocytes, PfNT1's ligand specificity, kinetic parameters, and inhibition profile are all sufficiently different from hENT1 to make it an attractive target for selective therapeutic drug design.

Synthesis of Phospholipids in Malaria Parasites

The protozoan parasite, *Plasmodium falciparum*, is the causative agent of the most severe form of human malaria, resulting in 300-500 million cases and 1-3 million deaths per year (World Health Organization (2000), *WHO Tech. Rep. Ser.* 892, 1-74). The pathogenic stages of *P. falciparum* are those that invade mature erythrocytes, which are devoid of internal organelles and incapable of de novo lipid biosynthesis. Despite this, *P. falciparum* undergoes dramatic morphological and metabolic developmental changes and asexually divides to form up to 36 new daughter cells within 48 hours of invading a human erythrocyte (Krishna, S. (1997), *BMF* 315, 730-732, 1997). This rapid multiplication of *P. falciparum* within host erythrocytes entails the active production of new plasma membranes in which phospholipids are major architectural and functional components. Phosphatidylcholine (PtdCho) and phosphatidylethanolamine (PtdEtn), comprise 40-50% and 35-45%, respectively, of the parasite's total plasma membrane phospholipid content (Vial, H. J., and Ben Mamoun, C. (2005), In: MOLECULAR APPROACHES TO MALARIA, I. W. Sherman, ed. (Washington D.C.: ASM Press), pp. 327-352).

Genome data predicts that *P. falciparum* possesses enzymatic pathways for the synthesis of all the necessary phospholipids from precursors transported from host milieu such as serine, choline, inositol, glycerol and fatty acids (Holz, G. G. (1977), *Bull. World Health Organ.* 55, 237-248; Vial and Ben Mamoun (2005), supra). The synthesis of PtdCho in *P. falciparum* takes place via two metabolic pathways, the de novo CDP-choline pathway (Kennedy pathway) and the serine-decarboxylation-phosphoethanolamine methylation (SDPM) pathway (FIG. 7). The latter is unique to *P. falciparum* and is absent in mammalian cells (Pessi, G., and Ben Mamoun, C. (2006), *Future Medicine, Future Lipidology* 1, 173-180; Pessi, G. et al. (2005), *J. Biol. Chem.* 280, 12461-12466; Pessi, G., et al., (2004), *Proc. Natl. Acad. Sci. U.S.A.* 101, 6206-6211). In the SDPM pathway, ethanolamine formed by the decarboxylation of serine by a parasite serine decarboxylase, is converted into phosphoethanolamine (p-Etn). The later serves as a precursor for the synthesis of PtdEtn through the CDP-ethanolamine pathway, and for the synthesis of PtdCho through the SDPM/CDP-choline pathways. Serine is readily available in the parasite cytosol due to the active degradation of host hemoglobin as well as uptake from the host milieu (Francis, S. E., et al., (1997), *J. Biol. Chem.* 272, 14961-14968; Kirk, K. (2001), *Physiol. Rev.* 81, 495-537).

The Role of PfPMT in Parasite Membrane Lipid Biogenesis

The PfPMT gene in *P. falciparum* encodes the phosphoethanolamine methyltransferase (PMT) that specifically methylates p-Etn to phosphocholine (p-Cho) via the SDPM pathway. P-Cho is then utilized by the CDP-choline pathway to synthesize PtdCho. The CDP-choline pathway also utilizes p-Cho synthesized from choline. PfPMT is a member of the PEAMT family of phosphoethanolamine methyltransferases whose members are also found in worms, plants, and other protozoa. The restricted phylogenetic distribution of the PEAMT family of phosphoethanolamine methyltransferases makes members of this class of enzymes excellent targets for drugs to treat malaria and other parasitic diseases.

It is shown herein that *P. falciparum* parasites lacking PfPMT are unable to synthesize their major phospholipid, PtdCho, via the SDPM pathway, and display severe alterations in parasite development, multiplication, survival and infectivity. These results indicate that PfPMT plays a key physiological role during the intraerythrocytic life cycle of the parasite, a property that can be exploited to develop novel antimalarial drugs and vaccines.

The results presented here using radiolabeled ethanolamine as a precursor showed that whereas wild type, complemented, and pfpmtΔ parasite strains synthesized PtdEtn from ethanolamine, only wild type and complemented parasites formed PtdCho from this precursor. These data thus demonstrate that the transmethylation of PtdEtn into PtdCho does not occur in *P. falciparum* and that the SDPM pathway is the only pathway used by the parasite to synthesize PtdCho from ethanolamine.

As described herein, loss of PfPMT also resulted in significant reduction (~50%) in parasite progeny that was only marginally rescued by choline supplementation even up to 25-fold the human physiological concentration of approximately 7-20 μM. This suggests that the SDPM pathway might be the most significant source of p-Cho used for the biosynthesis of PtdCho in *P. falciparum*.

Analysis of the rate at which the parasites progressed into schizogony by flow cytometry indicated that pfpmtΔ parasites had a delayed rate of nuclear division and formed fewer nuclei per infected erythrocyte than the wild-type and complemented parasites. Furthermore, of the parasites that progressed through the intraerythrocytic life cycle, a substantial percentage underwent DNA degradation as revealed by TUNEL staining. Treatment of wild-type parasites, which are uniformly TUNEL-negative, with lethal doses of chloroquine or pyrimethamine (all three strains are sensitive to these compounds) resulted in positive TUNEL staining, confirming that this assay measures parasite death. Together, these findings indicate that disruption of PfPMT results in defective parasite cellularization and reduced parasite viability.

In sum, as shown herein, disruption of the PfPMT gene in P. falciparum completely abrogates the parasite's ability to synthesize PtdCho from serine. The PfPMT gene plays an important role in membrane biogenesis, development, survival, and propagation of intraerythrocytic P. falciparum, as disruption of the gene dramatic decreases replication and cellularization and reduces survival of daughter merozoites. The data described herein thus reveal a new role for PfPMT in parasite proliferation, survival and virulence, and indicate that inhibition of PfPMT can be used as a strategy for developing new therapeutic strategies and vaccines for controlling malaria infection.

Embodiments of the Invention

The present application relates to the development and use of attenuated strains of malarial parasites as vaccines for the prevention and treatment of malaria. Moreover, the instant application is directed to a vaccine and methods of immunization targeted at the asexual (blood) phase of the malarial parasite's life, when the parasites are in red blood cells. The present application relates to a malaria vaccine for administration to a host, wherein the vaccine contains a malarial parasite with at least one non-functional gene that encodes a protein necessary for continued in vivo survival, proliferation and infection of host red blood cells by the parasite. The species of malarial parasites can include Plasmodium vivax, Plasmodium malariae, Plasmodium ovale and Plasmodium falciparum. Strains of P. falciparum can include the 3D7 strain, the Vietnam-Fort (FVO) strain, Uganda-Palo Alto (FUP) strain, FCH/4 (Philippines) strain, the falciparum Santa Lucia (Salvador I) strain and the Malayan Camp (MC) strain.

The present application also relates to malaria vaccines wherein a gene of the malarial parasite is rendered non-functional in which the gene, in its naturally occurring state, encodes a protein necessary for nutrition of the malaria parasite, including a parasite plasma membrane transporter, such as an essential nutrient transporter (e.g., a nucleoside transporter, in particular a purine transporter; a glucose transporter; an amino acid transporter). In the description herein, a gene which has been rendered non-functional by any method is sometimes referred to as a "non-functional gene."

The present application also relates to malaria vaccines wherein the gene(s) of the malarial parasite that is rendered non-functional by modification or deletion normally encodes a protein necessary for the formation of a component of the parasite's plasma membrane, such as a phospholipid. Phosphatidylcholine (PtdCho) and phosphatidylethanolamine (ptdEtn), comprise 40-50% and 35-45%, respectively, of the parasite's total plasma membrane phospholipid content.

In addition, the present application relates to a malaria vaccine wherein the non-functional gene of the malarial parasite is rendered non-functional by knockout technology and/or homologous recombination.

In one embodiment of the present application, the malaria vaccine is composed of a malarial parasite with two non-functional genes, which encode two proteins necessary for continued in vivo survival, proliferation and infection of host red blood cells by the parasite.

Another embodiment of the present application is a method for growing malarial parasites with at least one non-functional gene for use as vaccine, in which the method includes growth at non-physiological concentrations of choline or other essential nutrients. In one embodiment, parasites with a non-functional gene for an enzyme essential for the synthesis of PtdCho require choline concentrations in the range of at least about 200 μM to about 500 μM in order to grow and proliferate in vitro.

In another embodiment, parasites with a non-functional gene for an enzyme essential for the synthesis of PtdCho require choline concentrations in the range of at least about 50 μM to at least about 1 mM (e.g., at least about 100, 200, 300, 400, 500, 600, 700, 800, 900, or 1000 μM choline) in order to grow and proliferate in vitro. In a further optional embodiment, malarial parasites are isolated from the medium containing non-physiological (i.e., higher than physiological) choline concentrations and are exposed for a length of time to much lower, physiological concentrations of choline. Such exposure may confer advantages to the effectiveness and/or reliability of the resulting malaria vaccine, for example, by conferring a greater degree of control and predictability on the number of cell divisions the attenuated parasite undergoes following administration of malarial vaccine to a subject.

The malarial vaccines provided herein can be combined with pharmaceutically acceptable carriers and immunogenic adjuvants in accordance with methods known to those skilled in the art.

Still another embodiment of the present application relates to a method of eliciting an immune response in a host by introducing into the host any one of the malaria vaccines mentioned above in an amount sufficient to elicit an immune response. In one embodiment the host is a human and the vaccine is administered by injection.

DEFINITIONS

In the description that follows, a number of terms used in recombinant DNA, parasitology and immunology are extensively utilized. In order to provide a clear and consistent understanding of the specification and claims, including the scope to be given such terms, the following definitions are provided.

The term "eliciting an immune response" refers to the ability of a substance to cause a humoral and/or cellular response, whether alone or when linked to a carrier, in the presence or absence of an adjuvant.

"Neutralization" refers to an immune response that blocks the infectivity, either partially or fully, of an infectious agent.

A "vaccine" is an immunogenic composition, such as an attenuated parasite strain, capable of eliciting protection against malaria, whether partial or complete. A vaccine may also be useful for treatment of an infected individual, in which case it is called a therapeutic vaccine.

The term "therapeutic" refers to a composition capable of treating malaria infection.

The term "effective amount" for a therapeutic or prophylactic treatment refers to an amount of a malarial parasite sufficient to induce an immunogenic response in the individual to which it is administered. Preferably, the effective amount is sufficient to effect prevention or to effect treatment, as defined above. In one embodiment, an effective amount of the vaccine provided herein is directed to, or effective against, the blood-stage of malaria infection. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of numbers of malarial parasites for prophylaxis of malaria disease are about 10 to 1,000,000; for example, about 10,000 to 50,000 per dose. Several doses of vaccine may be needed per individual in order to achieve a sufficient immune response and subsequent protection against malaria.

In general, an "epitope" is defined as a linear array of 3-10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by two or more essential regions of subunits of a homo-oligomer or hetero-oligomer. As used herein, "epitope" or "antigenic determinant" means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, sub-type (or genotype), or type (group)-specific variants, e.g., of the currently known sequences or strains belonging to *Plasmodium* such as 3D7, FVO and MC, or any other known or newly defined *Plasmodium* strain.

The term "nucleobase" includes purines and pyrimidines.

Malarial Species and Strains

Malarial species relating to the compositions and methods described herein include *Plasmodium vivax, Plasmodium malariae, Plasmodium ovale* and *Plasmodium falciparum*. Particular strains of *P. falciparum* related to the present invention include the 3D7 strain, the Vietnam-Fort (FVO) strain, the Uganda-Palo Alto (FUP) strain, the FCH/4 (Philippines) strain, the falciparum Santa Lucia (Salvador I) strain and the Malayan Camp (MC) strain. Other *Plasmodium* species parasitize birds and non-human animals.

Nutrient Transporters

Genes for nutrient transporters that are related to the present invention and that are useful when made non-functional include genes for any transporters that are involved in the uptake of essential nutrients from human serum into malaria parasites when such parasites are present inside infected erythrocytes (blood-stage). Among these transporters are the purine transporter; the glucose transporter; amino acid transporter and the choline transporter.

Membrane Lipid Biogenesis

Genes necessary for membrane lipid biogenesis that are related to the present invention and that are useful when made non-functional include genes that when disrupted prevent the operation of a pathway that is involved in the synthesis of essential membrane lipids for malaria parasites when such parasites are present inside infected erythrocytes (blood-stage). Among these genes is PfPMT.

Knockout Technology

An important aspect of the present invention is a null mutation in the genes relating to the nutrition and/or membrane biogenesis of malarial parasites. One method of inhibiting the expression of these genes is to disrupt the gene in malarial parasite cells. This method is generally known as knockout technology.

In a general sense, preparation of a knockout requires first introducing a nucleic acid construct that will be used to suppress expression of a particular gene into a malarial parasite cell, where it is to be integrated into the parasite's genome at the appropriate location.

U.S. Pat. No. 5,616,491, incorporated herein by reference in its entirety, generally describes the techniques involved in the preparation of knockout genes. The term "knockout" refers to a partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of: (1) DNA from some portion of the gene (exon sequence, intron sequence, and/or promoter sequence) to be suppressed; and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA).

The knockout construct nucleic acid sequence may comprise (1) a full or partial sequence of one or more exons and/or introns of the gene to be suppressed, (2) a full or partial promoter sequence of the gene to be suppressed, or (3) combinations thereof. Typically, the knockout construct is inserted into malarial parasite cell and is integrated into the cell genomic DNA, usually by the process of homologous recombination.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

Usually, the DNA to be used in the knockout construct will be one or more exon and/or intron regions, and/or a promoter region from the genomic sequence provided herein, but may also be cDNA sequence. Generally, the DNA will be at least about 500 bp (base pairs) to 1 kilobase (kb) in length, and in certain aspects up to 3-4 kb in length, thereby providing sufficient complementary sequence for hybridization when the knockout construct is introduced into the genomic DNA of the cell.

Preparation and Formulation of Malarial Vaccines

As described herein, the attenuated malarial strains may be introduced into a host by injection or other routes of administration, in one or more administration events at different time points, thereby eliciting an immune response protective against malarial infection. In a further embodiment, the attenuated malarial strains and formulations employing the strains may be admixed in various combinations and or admixed with other known proteins, peptides, or adjuvants which are known or believed to facilitate an immunological response, thereby providing enhanced immunity. In an alternative embodiment, the components may be administered separately, i.e., at different time points, which is known or believed to facilitate an immunological response, thereby providing protection against malarial infection. For example, the attenuated strain can be combined with one or more antigens or toxoids, such as tetanus toxoid, diphtheria toxoid, cholera toxoid, ovalbumin (OVA), or keyhole limpet haemocyanin (KLH).

The pharmaceutically acceptable carriers which can be used include, but are not limited to, an excipient, a stabilizer, a binder, a lubricant, a colorant, a disintegrant, a buffer, an isotonic agent, a preservative, an anesthetic, and the like which are commonly used in a medical field.

Also, the dosage form, such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like, can be used appropriately depending on the administration method and the polypeptides described herein can be accordingly formulated. Pharmaceutical formulations are generally known in the art and are described, for example, in Chapter 25.2 of COMPREHENSIVE MEDICINAL CHEMISTRY, Volume 5, Editor Hansch et al, Pergamon Press 1990.

Also provided herein are compositions containing the attenuated strains thereof and one or more suitable adjuvants commonly used in the field of immunology and medicine to enhance the immune response in a subject. Examples of such adjuvants include monophosphoryl lipid A (MPL), a detoxified derivative of the lipopolysaccharide (LPS) moiety of Salmonella Minnesota R595, which has retained immunostimulatory activities and has been shown to promote Th1 responses when co-administered with antigens (see U.S. Pat. No. 4,877,611; Tomai et al., *Journal of Biological Response Modifiers*, (1987), 6:99-107; Chen et al., *Journal of Leukocyte Biology*, (1991), 49:416-422; Garg & Subbarao, *Infection and Immunity*, (1992), 60(6):2329-2336; Chase et al., *Infection and immunity*, (1986), 53(3):711-712; Masihi et al, *Journal of Biological Response Modifiers*, (1988), 7:535-539; Fitzgerald, *Vaccine*, (1991), 9:265-272; Bennett et al, *Journal of Biological Response Modifiers* (1988), 7:65-76; Kovach et al., *Journal of Experimental Medicine*, (1990), 172:77-84; Elliott et al., *Journal of Immunology*, (1991), 10:69-74; Wheeler A. W., Marshall J. S., Ulrich J. T., *International Archives of Allergy and Immunology*, (2001), 126 (2):135-9; and Odean et al., *Infection and Immunity*, (1990), 58(2):427-432); MPL derivatives (see U.S. Pat. No. 4,987, 237) other general adjuvants (see U.S. Pat. No. 4,877,611); CpG and ISS oligodeoxynucleotides (see U.S. Pat. No. 6,194, 388; U.S. Pat. No. 6,207,646; U.S. Pat. No. 6,239,116; U.S. Pat. No. 6,339,068; McCluskie, M. J., and H. L. Davis. Vaccine 2002. 19:413-422; Ronaghy A, Prakken B J, Takabayashi K, Firestein G S, Boyle D, Zvailfler N J, Roord S T, Albani S, Carson D A, Raz E. Immunostimulatory DNA sequences influence the course of adjuvant arthritis. *Journal of Immunology*, (2002), 168(1):51-6; Miconnet et al (2002) 168(3) *Journal of Immunology* pp 1212-1218; Li et al (2001) *Vaccine*, 20(1-2):148-157; Davis (2000) *Developmental Biology* 104:165-169; Derek T. O'Hagan, Mary Lee MacKichan, Manmohan Singh, Recent developments in adjuvants for vaccines against infectious diseases, Biomolecular Engineering 18 (3) (2001) pp. 69-85; McCluskie et al (2001) Critical Reviews in Immunology 21(1-3):103-120); trehalose dimycolate (see U.S. Pat. No. 4,579,945); amphipathic and surface active agents, e.g., saponin and derivatives such as QS21 (see U.S. Pat. No. 5,583,112); oligonucleotides (Yamamoto et al, *Japanese Journal of Cancer Research*, 79:866-873, 1988); detoxified endotoxins (see U.S. Pat. No. 4,866,034); detoxified endotoxins combined with other adjuvants (see U.S. Pat. No. 4,435,386); combinations with QS-21 (see U.S. Pat. No. 6,146,632); combinations of detoxified endotoxins with trehalose dimycolate and endotoxic glycolipids (see U.S. Pat. No. 4,505,899); combinations of detoxified endotoxins with cell wall skeleton (CWS) or CWS and trehalose dimycolate (see U.S. Pat. Nos. 4,436,727, 4,436,728 and 4,505,900); combinations of just CWS and trehalose dimycolate, without detoxified endotoxins (as described in U.S. Pat. No. 4,520, 019); chitosan adjuvants (see U.S. Pat. Nos. 5,912,000; 5,965, 144; 5,980,912; Seferian, P. G., and Martinez, M. L. Immune stimulating activity of two new chitosan containing adjuvant formulations (2001) *Vaccine*, (2000), 19(6):661-8). All of the references cited in this paragraph are incorporated herein by reference.

In another embodiment, various adjuvants, even those that are not commonly used in humans, may be employed in animals where, for example, one desires to subsequently obtain activated T cells or to protect valuable or valued animals from infection due to malarial infections.

Administration of Vaccines

As used herein the subject that would benefit from the administration of the attenuated vaccines and formulations described herein include any host that can benefit from protection against malarial infection. In one embodiment, the subject is a human. In another embodiment, the subject is a domestic animal, including but not limited to dog, cat, horse, bovine (meaning any sex or variety of cattle) or other such domestic animals. In another embodiment, the subject is a non-human primate or an animal known to be or proposed to be an animal model of human malarial infection.

By providing an attenuated vaccine capable of eliciting an immune response in a subject human, including vaccination, the invention covers any strain of *Plasmodium* incapable of conversion to the parasitic, disease-causing virulent phase but that induces an immune reaction that results in or augments the subject's level of immune protection against malarial infection.

As used herein, "inhibit", "inhibiting" or "inhibition" includes any measurable or reproducible reduction in the infectivity of a malarial strain in the subject host. "Reduction in infectivity" means the ability of the subject to prevent or limit the spread of the malarial strain in red blood cells and tissues or organs exposed or infected by said malarial parasite. Furthermore, "amelioration", "protection", "prevention" and "treatment" mean any measurable or reproducible reduction, prevention, or removal of any of the symptoms associated with malarial infectivity, and particularly, the prevention, or amelioration of *P. falciparum* infection and resultant pathology itself.

The dosages of the attenuated vaccines used to provide immunostimulation include from about 10 to about 1,000,000 malarial parasite cells, inclusive of all ranges and subranges there between, e.g., but not limited to, about 100 to about 100,000 malarial parasite cells, about 500 to about 50,000 malarial parasite cells, about 1,000 to about 10,000 malarial parasite cells, about 100 to about 1,000 malarial parasite cells, etc., as will be understood by the skilled artisan. Such amount may be administered as a single dosage or may be administered according to a regimen, including subsequent booster doses, whereby it is effective; e.g., the compositions of the present invention can be administered one time or serially over the course of a period of days, weeks, months, and/or years.

The compositions of the attenuated vaccines can be administered by any suitable administration method including, but not limited to, injections (subcutaneous, intramuscular, intracutaneous, intravenous, intraperitoneal), oral administration, intranasal administration, inhalation, or other methods of instillation known in the art.

Kits

Also included within the scope of the present invention are kits suitable for providing compositions of the attenuated vaccines. For example, in such a kit one vial can comprise the attenuated malarial strain of the invention admixed with a pharmaceutically acceptable carrier, either in a aqueous, non-aqueous, or dry state; and a second vial which can carry immunostimulatory agents, and or a suitable diluent for the composition, which will provide the user with the appropriate concentration of malarial parasite to be delivered to the host. In one embodiment, the kit will contain instructions for using the composition and other components, as included; such instructions can be in the form of printed, electronic, visual, and or audio instructions. The vaccinations will normally be at from two to twelve week intervals, more usually from three to five week intervals. Periodic boosters at intervals of 1-5 years, usually three years, will be desirable to maintain protective levels. The course of the immunization may be followed by assays for activated T cells produced, skin-test reactivity, or other indicators of an immune response to a malarial strain.

Having generally described the attenuated strains of malarial strains useful as vaccines and the methods to create and administer them to elicit protective immune responses, a further understanding can be obtained by reference to certain specific examples that are provided herein for purposes of illustration only, and are not intended to be limiting unless otherwise specified.

All publications and patent applications cited in this specification are herein incorporated by reference as if each individual publication or patent application were specifically and individually indicated to be incorporated by reference in its entirety.

EXAMPLES

Example 1

Materials and Methods for Disruption of PfNT1 Expression

Construction of Transfection Plasmids

To construct the targeting vector pRZ/TK/PfNT1.5'-BSD-PfNT1.3' for PfNT1 disruption, a 482 bp fragment (nucleotides 50-532 of the open reading frame (ORF)) of PfNT1 was amplified by polymerase chain reaction (PCR) and subcloned into the HindIII/BlpI site upstream of the PcDT promoter in the pRZ-TK-BSD2 vector. This plasmid encompasses the positive selectable marker blasticidin-s-deaminase (BSD) (Mamoun, C. B., Gluzman, I. Y., Goyard, S., Beverley, S. M. & Goldberg, D. E. (1999) *Proc Natl Acad Sci USA*, 96, 8716-20) from *Aspergillus terreus* that confers resistance to blasticidin and whose expression in *P. falciparum* is under the regulatory control of the *P. chabaudi* DHFR/TS promoter and the negative marker thymidine kinase (TK) from Herpes simplex that confers sensitivity to ganciclovir and whose expression is under the regulatory control of the *P. falciparum* CAM promoter. A second PCR was used to amplify a 482 bp fragment (nucleotides 772-1255 of the ORF) of PfNT1 for directional cloning at the EcoRI site downstream of the HrpII terminator in the pRZ-TK-BSD2 vector.

Disruption of the PfNT1 Locus

Packed *P. falciparum* strain 3D7 infected human red blood cells (RBCs) (100 µl) were mixed with ~100 µg of plasmid DNA in 400 µl of cytomix and electroporated at 0.31 kV and 950 µF in a 0.2-cm cuvette using a Gene Pulser II (Bio-Rad). After 48 h, 2.5 µg/ml blasticidin was added. Blasticidin-resistant parasites were observed after 3 weeks. To eliminate parasites containing episomes, ganciclovir, a subversive substrate of the TK enzyme, was applied for an additional three weeks. Surviving parasites were cloned by limiting dilution. Note that parasites were cultured as described (Trager, W. & Jensen, J. B. (1976) *Science*, 193, 673-5), except that 1.5 mM hypoxanthine was added to the medium for transfectants.

Southern Hybridization of the Disrupted PfNT1 Locus

Ten micrograms of genomic DNA from wild-type and pfnt1Δ parasites was digested with Xba I and Hind III, separated on a 0.8% agarose gel, and transferred to positively charged nylon membrane (Roche Molecular Biochemicals). Membranes were probed with [$\alpha$-$^{32}$P]dCTP-labeled PfNT1 and BSD probes.

Western Blot Analysis

Western analysis was performed as described (Rager, N., Mamoun, C. B., Carter, N. S., Goldberg, D. E. & Ullman, B. (2001) *J Biol Chem*, 276, 41095-9; Santiago, T. C., Zufferey, R., Mehra, R. S., Coleman, R. A. & Ben Mamoun, C. (2004) *J Biol Chem*, 279, 9222-32) on protein extracts from asynchronous cultures of wild-type and pfnt1Δ strains. Blots were probed with affinity-purified antibodies to PfNT1 (1:1000) and glycerol-3-phosphate acyltransferase, PfGat (1:1000), a marker which served as a loading control.

Microscopy

To determine parasite life cycle stage, infected-RBCs were Giemsa-stained and analyzed by bright-field microscopy. For immunofluorescence microscopy, asynchronous cultures of *P. falciparum* were prepared essentially as previously described (Rager, N., Mamoun, C. B., Carter, N. S., Goldberg, D. E. & Ullman, B. (2001) *J Biol Chem*, 276, 41095-9). Coverslips were incubated at room temperature with gentle shaking for 1 h with both affinity-purified PfNT1 antibodies at a concentration of 1:500 (Rager) and mouse monoclonal antibodies to erythrocyte Band 3 protein from Sigma, which were used at a concentration of 1:500. The coverslips were washed to remove excess antibody and incubated with anti-rabbit antibody conjugated to fluorescein isothiocyanate (FITC) and anti-mouse secondary antibody conjugated to Texas red dye (Molecular Probes) for 1 h at room temperature to visualize the PfNT1 and Band 3 antibodies. Nuclei were stained by incubating the coverslips in phosphate buffered saline (PBS) containing 3 µg/ml of Hoechst stain (Molecular Probes) for 5 min at room temperature. The coverslips were washed and then mounted on slides with Antifade (Molecular Probes) and images analyzed by high-resolution fluorescence using deconvolution protocols. Microscopy was performed with a Nikon eclipse TE2000-E microscope using filter 96320/HYQ (ex. 480-440/em. 440) for FITC, 96312/G2EC (ex. 540-525/em. 620-660) for Rhodamine, and 96310/UV2EC (ex. 360-340/em. 460-450) for DAPI.

Parasite Lactate Dehydrogenase Assay for Detecting Parasites

The reagents for the parasite lactate dehydrogenase (LDH) assay, 3-acetylpyridine adenine dinucleotide (APAD), nitroblue tetrozolium (NBT), and diaphorase, were obtained from Sigma-Aldrich (St. Louis, Mo.). The malstat reagent was prepared by mixing 13 mg/ml of Tris-Cl pH 9.0, 20 mg/ml of lithium L-lactate, 0.66 mg/ml of 3-acetylpyridine NAD (APAD), and 0.2% Triton X-100. To perform the pLDH assay, 20 μA of infected RBCs were mixed with 10 μl of 1 mg/ml diaphorase, 10 μl of 1 mg/ml NBT, and 100 μl of malstat reagent in each well of the 96-well plate. The absorbance was measured at 650 nm using a plate reader and was always proportional to the parasitemia detected by Giemsa-stained blood smears.

Uptake Assays of Nucleosides and Nucleobases on Free Trophozoites

Wild-type and pfnt1Δ-infected RBCs were synchronized using sorbitol (Lambros, C. & Vanderberg, J. P. (1979) *J Parasitol*, 65, 418-20) and trophozoites harvested by centrifugation at 720×g for 5 min at 4° C. The cell pellet was gently resuspended in cold PBS containing 0.005% saponin and again centrifuged as described above. The pellet was washed three times in cold PBS, resuspended in cold PBS supplemented with 20 mM glucose, and used immediately for transport assays. The cells were incubated with either 1 μM [$^3$H] adenosine (40.3 Ci/mmol), [$^3$H]inosine (50 Ci/mmol), [$^3$H] hypoxanthine (30 Ci/mmol), [$^3$H]guanine (11.8 Ci/mmol), or [$^3$H]isoleucine (92 Ci/mmol) at 37° C. or 4° C. for 1.5 min (linear phase of uptake), after which they were rapidly applied to glass fiber filters and washed twice with 5 ml of cold PBS. Filters were dried and counted by scintillation spectrometry.

Example 2

Disruption of the PfNT1 Gene in pKEΔPfNT Parasites

To evaluate the importance of PfNT1 in parasite development and survival, the generation of transgenic parasites lacking PfNT1 was attempted by a targeted gene replacement approach (Duraisingh, M. T., Triglia, T. & Cowman, A. F. (2002) *Int J Parasitol*, 32, 81-9). To achieve this goal, a targeting vector pKEΔPfNT was constructed (FIG. 1A). The overall knockout strategy entails a two step process by which PfNT1 is first interrupted with the blasticidin-s-deaminase (BSD) (Mamoun, C. B., Gluzman, I. Y., Goyard, S., Beverley, S. M. & Goldberg, D. E. (1999) *Proc Natl Acad Sci USA*, 96, 8716-20) cassette after a double cross-over event (FIG. 1A) followed by loss of the episome after selection against thymidine kinase (TK) gene expression. This targeted gene disruption strategy with double cross-over caused a 255 bp truncation in the middle of the PfNT1 open reading frame (ORF). Since loss of PfNT1 was conjectured to be a potentially lethal event (if PfNT1 is the major route of purine salvage in *P. falciparum*), pfnt1Δ mutants were selected in medium supplemented with 1.5 mM hypoxanthine, a concentration ~300-fold above that required for optimal growth of wild-type parasites. Transgenic parasites harboring the pKEΔ-PfNT targeting vector were first selected on blasticidin, then were treated with ganciclovir to eliminate parasites containing the targeting cassette in an episomal form. Parasites were cloned by limiting dilution and genomic DNA from cloned parasites purified for molecular analysis. Diagnostic PCR analysis using various combinations of primer pairs demonstrated the integration of the PfNT1.5'-BSD-PfNT1.3' cassette into the PfNT1 locus and the absence of intact wild type PfNT1 in 59 individual clones. Southern blot analyses on genomic DNA using various restriction digestions and probes specific for PfNT1 or BSD further confirmed disruption of the PfNT1 chromosomal locus by a double cross over event (FIG. 1B).

Example 3

Loss of Expression of PfNT1 in the pfnt1Δ Knockout

To demonstrate the loss of PfNT1 expression in a pfnt1Δ clone, RT-PCR analysis was performed on RNA purified from wild-type and knockout parasites using primers within the PfNT1 ORF. PfNT1 cDNA was amplified from wild-type but not pfnt1Δ RNA (FIG. 2A). Loss of PfNT1 expression was further analyzed by immunoblotting using affinity-purified anti-PfNT1 antibodies (Rager, N., Mamoun, C. B., Carter, N. S., Goldberg, D. E. & Ullman, B. (2001) *J Biol Chem*, 276, 41095-9). Whereas a 46 kDa PfNT1 band was detected in wild-type *P. falciparum*, no signal was identified in the pfnt1Δ parasites (FIG. 2B). As a loading control, antibodies raised against the parasite endoplasmic reticulum membrane protein PfGat (Santiago, T. C., Zufferey, R., Mehra, R. S., Coleman, R. A. & Ben Mamoun, C. (2004) *J Biol Chem*, 279, 9222-32) were used, and the expected 64 kDa PfGat band was observed in both the wild-type and pfnt1Δlysates (FIG. 2B). Immunofluorescence analysis corroborated the loss of PfNT1 expression in the pfnt1Δ clone and verified its localization to the PPM in wild type *P. falciparum* (FIG. 2C) (Rager, N., Mamoun, C. B., Carter, N. S., Goldberg, D. E. & Ullman, B. (2001) *J Biol Chem*, 276, 41095-9).

Example 4

Purine Requirements for pfnt1Δ Parasites

To assess the role of PfNT1 in purine acquisition during the parasite intraerythrocytic life cycle, wild-type and pfnt1Δ *P. falciparum* were grown in the presence of increasing concentrations of hypoxanthine, adenosine or inosine, and parasite growth was monitored by measuring parasite LDH production. Whereas optimal growth was observed in wild-type parasites at purine concentrations of 5 μM and above, pfnt1Δ parasites were not viable in adenosine, inosine, or hypoxanthine at concentrations below 50 μM (FIG. 3A). To measure the impact of the pfnt1Δ lesion on parasite intraerythrocytic development, wild-type and pfnt1Δ cells were synchronized and cultured in the absence or presence of increasing concentrations of hypoxanthine. Parasite progression through the life cycle (ring>trophozoite>schizont>ring) was monitored at various times after erythrocyte invasion. For both strains lack of purine resulted in blockage of growth at the ring stage (FIG. 3B). However, whereas wild-type *P. falciparum* completed their entire intraerythrocytic cycle at concentrations of hypoxanthine as low as 2 μM (FIG. 3B), pfnt1Δ mutants required significantly higher concentrations of hypoxanthine to progress from the ring stage of development (FIG. 3B). Similar results were obtained with adenosine and inosine. Concentrations of hypoxanthine between 100 μM and 1.5 mM restored parasite progression throughout the cell cycle, although the growth of pfnt1Δ was slower than that of the wild-type strain at concentrations below 500 μM. These results demonstrate that under physiological purine concentrations (between 0.4 and 6 μM (Traut, T. W. (1994) *Mol Cell*

Biochem, 140, 1-22)). PfNT1 is essential for the intraerythrocytic development of the parasite and that at higher concentrations hypoxanthine, adenosine and inosine could be transported via a secondary mechanism. Parasite utilization of adenosine and inosine could be either via direct transport of these substrates or via conversion of the nucleosides into hypoxanthine by the sequential actions of ADA and PNP, respectively, prior to hypoxanthine uptake via PfNT1 (see below).

Example 5

Transport of Purines by pfnt1Δ Parasites

The inability of pfnt1Δ to grow at physiological concentrations of purine suggests that PfNT1 is the major route of purine translocation across the PPM. To test this supposition, both wild-type and pfnt1Δ parasites were purified from erythrocytes and their ability to transport radiolabeled hypoxanthine, adenosine, and inosine measured. Whereas the transport of adenosine and inosine was only diminished slightly in the pfnt1Δ strain, the transport of hypoxanthine was dramatically reduced when compared to its wild-type parent (FIG. 4). These differences in transport between wild-type and pfnt1Δ parasites did not arise from general discrepancies in translocation across the PPM since transport of isoleucine was identical in both strains (FIG. 4). The ability of erythrocyte-liberated pfnt1Δ parasites to effectively transport adenosine and inosine demonstrates that the PPM harbors one or more additional permeases capable of transporting these nucleosides.

Example 6

PfNT1 is Essential for Intraerythrocytic Development but not for Erythrocyte Invasion To determine whether the pfnt1 lesion is deleterious to *P. falciparum* parasites at all stages of intraerythrocytic development, wild-type and pfnt1Δ strains were synchronized and transferred at either ring, trophozoite or schizont stage from medium containing 100 μM of hypoxanthine to medium containing 5 μM hypoxanthine and their continued development monitored. While wild-type parasites exhibited normal progression from stage to stage throughout their entire intraerythrocytic development, pfnt1Δ parasites failed to transform from ring to trophozoite or from trophozoite to schizont stage (FIG. 5). The reduction in exogenous hypoxanthine concentration did not affect, however, the ability of pfnt1Δ merozoites to invade new erythrocytes following the rupture of infected erythrocytes during schizogony (FIG. 5).

Example 7

Materials and Methods for Disruption of PfPMT Expression

Construction of Transfection Plasmids

The plasmid pRZ-TK-BSD2 (El Bissati, K., et al. (2006), *Proc. Natl. Acad. Sci. U.S.A.* 103, 9286-9291) was used to construct the targeting vector pW-pfpmtΔ (FIG. 2). The pRZ-TK-BSD2 plasmid encompasses the positive selectable marker blasticidin-s-deaminase (BSD) (Mamoun, C. B., et al. (1999), *Proc. Natl. Acad. Sci. U.S.A.* 96, 8716-8720) from *Aspergillus terreus* that confers resistance to blasticidin and whose expression in *P. falciparum* is under the regulatory control of the *P. chabaudi* DHFR/TS (PCDT) promoter. The plasmid also harbors the negative marker thymidine kinase (TK) from Herpes simplex that confers sensitivity to ganciclovir and whose expression is under the regulatory control of the *P. falciparum* CAM promoter. To construct the targeting vector pW-pfpmtΔ for PfPMT gene disruption, a 601 bp fragment (nucleotides 18-619 of the unspliced PfPMT gene sequence) was amplified by PCR and cloned at the HindIII/BlpI site upstream of the PcDT promoter in the pRZ-TK-BSD2 plasmid. A second PCR was used to amplify a 505 bp fragment (nucleotides 650-1155 of the unspliced PfPMT gene sequence) for directional cloning at the EcoRI/NarI site downstream of the HrpII terminator in the pRZ-TK-BSD2 plasmid. A PfPMT-add-back vector for pfpmtΔ complementation was generated by PCR amplification of the 801 bp full coding sequence of PfPMT from *P. falciparum* total cDNA. The fragment was directionally cloned at the XhoI site of a pHC1 plasmid downstream the *P. falciparum* CAM promoter. The pHC1 vector harbors a *Toxoplasma gondii* dihydrofolate reductase gene that confers resistance to the selection drug, Pyrimethamine (Crabb, B. S., et al. (1997), *Mol. Biochem. Parasitol.* 90, 131-144).

Parasites and Transfection

*P. falciparum* strain 3D7 was cultured in human RBCs by the method of Trager and Jensen (Trager, W., and Jensen, J. B. (1976), *Science* 193, 673-675). Parasite transfection was done by mixing about 100 μg of plasmid DNA dissolved in 400 μl of cytomix with 100 μl of packed RBCs in a 0.2-cm cuvette followed by electroporation using a Gene Pulser II (Bio-Rad) set at 0.31 kV and 950 μF (Fidock, D. A., et al., (1998), *Mol. Pharmacol.* 54, 1140-1147). After transfection, the cultures were maintained for an initial 48 h without blasticidin and, thereafter, the drug was introduced in the cultures at 2.5 μg/ml final concentration. Cultures were continuously supplemented with 200 μM choline. Growth of blasticidin-resistant parasites commenced after 21 days of continuous drug selection. Genomic DNA was extracted from blasticidin-resistant parasites and analyzed for chromosomal integration of the plasmid by Southern blotting and PCR analysis.

To eliminate parasites containing the episomal plasmid, addition of blasticidin to the cultures was suspended for three weeks. Blasticidin was then reintroduced together with ganciclovir, a subversive substrate of the TK enzyme, and applied for three weeks. Clonal populations of the parasites were obtained by limiting dilution and used for genotypic and phenotypic characterizations. PfPMT gene disruption at the chromosomal locus was analyzed using the primer pair PfPMT-F (5'-ATGACTTTGATTGAAAACT-TAAACTCTG-3' (SEQ ID NO: 1)) and PfPMT-R (5'-TTTG-GTGGCCTTAAAATAACCCCATCTTTGCA-3' (SEQ ID NO: 2)).

Southern Hybridization

Genomic DNA was extracted from wild type and transfected parasites as previously described (Mamoun, C. B., et al., (1999), *Proc. Natl. Acad. Sci. U.S.A.* 96, 8716-8720). About 2.5 μg of the genomic DNA was digested with HindIII, fractionated on a 1% agarose gel and blotted onto a Nytran® SuperCharge Nylon membrane (Whatman Schleicher and Schuell). Membranes were probed with [α-$^{32}$P]dCTP-labeled PfPMT and BSD gene probes.

Western Blot Analysis

Parasites were extracted from infected erythrocytes by treatment with 0.15% saponin and sonicated in PBS. The soluble fraction was mixed with sodium dodecyl sulphate (SDS) sample buffer, boiled, fractionated on a 12% SDS-polyacrylamide gel, and transferred to a nitrocellulose membrane. Immunoblotting was done using affinity purified anti- PfPMT and anti-PfEF-1α antibodies as previously described (Witola, W. H., et al. (2006), *J. Biol. Chem.* 281, 21305-21311).

Reverse Transcriptase PCR

Asynchronous parasites were extracted from infected erythrocytes by saponin treatment and total RNA extracted by the Trizol reagent (Invitrogen). For each sample, 1 µg of total RNA was treated with Dnase I (Invitrogen) to remove any contaminating DNA followed by reverse transcription. PCR amplification of PfPMT from the transcribed parasite total cDNA was performed using the primer pair PfPMT-F and PfPMT-R. As a loading control, the cDNA of PfTPXI gene (PF14_0368 in PlasmoDB 4.4) was amplified.

Immunofluorescence Assays

Immunofluorescence assays were performed essentially as previously described (Witola et al., supra). Briefly, smears of asynchronous parasites were fixed with 1% formaldehyde and after permeabilization and blocking, smears were probed with a mixture of either rabbit mono-specific anti-PfPMT (1:50 dilution) or rabbit anti-PfNT1 (1:50) and mouse anti-erythrocyte Band3 (1:500 dilution) antibodies. Fluorescent anti-rabbit-FITC and anti-mouse-Texas Red antibodies at 1:500 dilution were used as secondary antibodies. Nuclei were stained with Hoechst stain (Molecular Probes). Mounted slides were analyzed using a Nikon eclipse TE2000-E microscope with filters 96320/HYQ (ex. 480-440/em. 440) for FITC, 96312/G2EC (ex. 540-525/em. 620-660) for Rhodamine, and 96310/UV2EC (ex. 360-340/em. 460-450) for DAPI. The same exposure times and other acquisition and processing parameters were used on all samples for both the wild type and mutant parasites.

PfPMT Enzyme Activity Assay

Synchronous parasites grown to 12% parasitaemia at the trophozoite stage, were extracted by saponin treatment. The parasite pellet was sonicated in extraction buffer (100 mM Hepes-KOH, pH7.8; 5 mM Dithiothreitol; 2 mM $Na_2EDTA$; 10% glycerol v/v) and the soluble fraction obtained by centrifugation. The reaction mixture contained 100 mM Hepes-KOH, pH 8.6; 2 mM EDTA; 10% glycerol; 2 mM S-adenosyl-L-methionine (SAM); 80 µM [methyl-$^{14}$C]-SAM (400 nCi) and 50 µg of parasite protein extract in a total reaction volume of 100 µl. A blank reaction mixture lacked protein extract. The reaction mixtures were incubated for 30 min at 30° C. and terminated by addition of 1 ml ice-cold water. The product was purified through a AG ($H^+$) resin following the method of Nuccio et al. (2000) and the product quantified by liquid scintillation counting.

Labeling Assays and Phospholipid Analysis

Synchronized parasites cultured in medium without choline at 2% hematocrit were grown to 10% parasitemia at early trophozoite stage. The parasitized erythrocytes were resuspended in fresh medium containing either 1.6 µCi (final concentration) [$^{14}$C]-ethanolamine hydrochloride or 0.1 µCi [$^{14}$C]-choline chloride and cultured for 12 h. The infected erythrocytes were washed twice with PBS and the pellet from a 60 ml culture volume was resuspended in 20× volume of chloroform/methanol (2:1, v/v). Lipids were extracted by the Folch method (Folch, J., et al. (1957), *J. Biol. Chem.* 226, 497-509) and the organic phase of the extract evaporated and redissolved in 600 µl of chloroform/methanol (2:1). The organic extract (150 µl) was fractionated by 2-dimensional thin layer chromatography (TLC) on Silica gel-60 20×20 cm plates (Merck). For the first dimension a solvent containing chloroform/methanol/ammonium hydroxide (84.5:45:6.5) was used. The second solvent was composed of chloroform/glacial acetic acid/methanol/water (90:30:6:2.6).

Parasite Growth Assays

Synchronized parasites at early ring stage were seeded at 2% parasitemia and cultured in the presence of 0, 10, 50, 100, 200 or 500 µM choline chloride for 96 h. Giemsa smears of the cultures were prepared at time points of 0, 12, 18, 32, 42, 56 and 96 h of culture and the parasite counts and morphological state determined by light microscopy. The parasite lactate dehydrogenase (pLDH) assay for quantifying parasites was performed at 48 h of culture (Makler, M. T., et al. (1993), *Am. J. Trop. Med. Hyg.* 48, 739-741). The reagents for the pLDH assay, 3-acetylpyridine adenine dinucleotide (APAD), nitroblue tetrozolium (NBT), and diaphorase, were obtained from Sigma-Aldrich (St. Louis, Mo.). The malstat reagent was prepared by mixing 13 mg/ml of Tris-Cl pH 9.0, 20 mg/ml of lithium L-lactate, 0.66 mg/ml of 3-acetylpyridine NAD (APAD), and 0.2% Triton X-100. To perform the pLDH assay, 20 µl of infected RBCs were mixed with 10 µl of 1 mg/ml diaphorase, 10 µl of 1 mg/ml NBT, and 100 µl of malstat reagent in each well of a 96-well plate. The absorbance was measured at 650 nm using a plate reader.

Flow Cytometric Analysis

Synchronized parasite cultures at 7% parasitemia with mostly early ring stage parasites were grown to mid-trophozoite stage. Starting when they were at the mid-trophozoite stage, samples were taken at time points of 0, 2, 4, 6, 8, 10, and 12 h, fixed with 0.5% (v/v) formaldehyde in PBS and kept at 4° C. The parasite nuclei were stained with 40 µg/ml Hoechst stain at room temperature for 30 min and washed twice with PBS. The parasitized erythrocytes were then resuspended in PBS to a final concentration of $1 \times 10^6$ cells/ml and analyzed by fluorescence activated cell sorting (FACS) to quantify the intensity of Hoechst fluorescence as a determinant of parasite nuclei content. One million cells were sorted per sample.

TdT-Mediated dUTP Nick End Labeling (TUNEL) Assay

The terminal deoxynucleotidyl transferase (TdT) dUTP nick end labeling (TUNEL) kit (Roche) was used to detect apoptotic cells following the manufacturer's instructions, with some modifications. Briefly, asynchronous cultures were grown to 10% parasitemia and 1 ml of the culture aliquots were washed twice with PBS and the cell count adjusted to $1 \times 10^6$ cells/ml. Fixation was achieved by resuspending the cells in 2% paraformaldehyde solution in PBS and incubated at room temperature for 1 h. The fixed cells were washed twice with PBS, resuspended in 100 µl of 0.1% Triton X-100 in 0.1% sodium citrate solution, and incubated for 2 min on ice. Cells were then washed twice in PBS and kept on ice until labeling. A positive control sample was prepared by incubating fixed and permeabilized cells with 3000 U/ml of DNase I for 15 min at room temperature followed by two washes with PBS. To label the cells, 50 µl of the TUNEL reaction mixture was added to the cell pellet and mixed gently. A negative control sample was included by treating fixed, permeabilized cells with the labeling solution in, the absence of the terminal TdT enzyme. The reaction mixtures were incubated in the dark at 37° C. for 1 h and then washed twice in PBS and resuspended in 250 µl PBS. Cells were analyzed by fluorescence microscopy at 525 nm wavelength with the FITC filter. To determine whether cells that reacted positively to the TUNEL staining corresponded to dying or dead parasites, parasites were grown in medium containing either 100 nM chloroquine or 100 nM pyrimethamine for 24 h and then processed for the TUNEL assay as described above.

Nuclei Counting by Spinning Disk Confocal Microscopy Using Synchronized Schizonts Counting of nuclei by SDCM was essentially as previously described for other strains of *P. falciparum* (Gligorijevic, B., et al. (2008), *Mol. Biochem. Parasitol.* 159:7-23). In brief, all cultures were first synchronized three times by 5% D-sorbitol treatment since multiple synchronization treatments successively improve the ring: early trophozoite ratio (Gligorijevic, B. et al. (2008), supra). Data were then routinely obtained 35-38 hrs after the last synchronization step, wherein segmented schizonts are clearly visible by light microscopy. The customized SDCM apparatus has been previously described in detail (Gligorijevic, B. et al. (2006), *Biochemistry* 45, 12400-12410; Gligorijevic, B. et al. (2008), supra). This instrument acquires "z stacks" for live cells at ~210-220 nm resolution (x, y and z) in less than 1 second, which eliminates blurring due to parasite movement within the malaria-infected red blood cells (iRBC). Along with reduced photobleaching and improved deconvolution procedures (Gligorijevic, B. et al. (2006), supra; Gligorijevic, B. et al. (2008), supra) the method provides a reliable and convenient way to count nuclei for live intraerythrocytic schizonts. A Merzhauser motorized MS-2000 XY translation stage and an additional piezo table optimized Z-movement (5 min/s over a range of 100 μm). Oil was DF-type (n=1.515, low background fluorescence), and the camera was a Hamamatsu ORCA ER cooled CCD with 1.3 Mpixel full frame and 8.9 fps full rate. Excitation of SybrGreen labelled nuclei (Gligorijevic, B. et al. (2008), supra) was with a Coherent Innova 300 I Ar/Kr laser (300 mW at 488 nm). Exposure was 100 ms at 100 mW laser power and z-spacing was 200 nm (appropriate for iterative deconvolution as in (Gligorijevic, B. et al. (2008), supra). After iterative deconvolution using experimentally derived point spread functions, the x, y resolution of fluorescence SDCM data is only slightly lower than that of classical LSCM confocal data (measured on our instrument to be 213 nm using 520 nm light). "Z stack" data were transferred to a Dell mini tower customized with three 750 Gb RAID array hard drives, and restoration was done using an Imaris 5.0.1/AutoQuant X software package from Bitplane Inc. (Saint Paul, Minn.) as described (Gligorijevic, B. et al. (2008), supra). Z-series of optical sections were deconvolved using the MLE method and a fixed PSF routine with 15 iterations. PSF were obtained by mixing subresolution (d=0.17 μm) fluorescent beads in cell culture. Restored images were transferred to Imaris and sorted into freely rotating three-dimensional objects in the 'Surpass' mode and nuclei counts were done with the aid of the "Spots" routine which locates fluorescence peaks in 3D space at operator defined contrast half-width and intensity. Assignment of 3D peaks as due to nuclei was confirmed by eye and then done in a semi-automated fashion to average across >200 schizonts in each case. Counts were exported to Excel or SigmaPlot software 9.0 for further statistical analysis.

Example 8

Disruption of the PfPMT Gene in PW-pfpmtΔ Parasites

To assess the physiological role of PfPMT in *P. falciparum*, we disrupted the PfPMT gene by homologous recombination. The targeting vector pW-PfPMTΔ (FIG. 8A) was generated using the pRZ-TK-BSD2 plasmid (El Bissati, K., et al. (2006), *Proc. Natl. Acad. Sci. USA* 103, 9286-9291). The overall knockout strategy (FIG. 8A) involved a two-step process by which the chromosomal PfPMT locus was first disrupted with the BSD cassette, after double cross-over homologous recombination, followed by elimination of the episome by selecting against expression of the TK gene. To avoid loss of the knockout parasites within the population (in the event that the SDPM pathway is an essential route for PtdCho biosynthesis), transfected parasites were continuously cultured in the presence of a concentration of choline (200 μM) choline ~20-fold greater than that present in human serum (Zeisel, S. H. (2000), *J. Am. Coll. Nutr.* 19, 528S-531S; Zeisel, S. H., et al. (1980), *Neurology* 30, 1226-1229).

Transgenic parasites harboring the pW-pfpmtΔ targeting vector were first selected on blasticidin and later treated with ganciclovir to eliminate parasites containing the targeting cassette in an episomal form. Parasites were cloned by limiting dilution and genomic DNA from cloned parasites purified for molecular analysis. Diagnostic PCR analysis using various combinations of primer pairs, demonstrated the replacement of the PfPMT gene by the BSD-containing targeting cassette in 10 individual clones. Southern blotting of HindIII-digested genomic DNA isolated from one clone (e.g. FIG. 8B), and using a 601 bp 5'-end PfPMT gene fragment probe (identical in sequence to that cloned in the pW-pfpmtΔ vector), showed the presence of 5.6 kb and 9.3 kb fragments in the pfpmtΔ and wild type parasites, respectively, confirming the disruption of the PfPMT gene locus in the pfpmtΔ parasites (FIGS. 8B and C). Additionally, probing with the BSD gene fragment revealed the expected 5.4 kb fragment in the pfpmtΔ parasites but not wild type (FIG. 8C), further confirming that gene replacement had occurred.

Example 9

Loss of Expression of PfPMT in the PfPMT Knockout

To test the loss of PfPMT expression in the selected pfpmtΔ clone, RT-PCR analysis was performed using primers within the PfPMT open reading frame. PfPMT cDNA could be detected using wild type, but not pfpmtΔ RNA (FIG. 8D). Analysis of the loss of PfPMT expression by immunoblotting using affinity-purified anti-Pfpmt antibodies showed that, whereas a 30 kDa Pfpmt band was detectable in the wild type strain, there was no signal in the knockout strain (FIG. 8E). As a loading control, antibodies raised against the parasite translation elongation factor PfEF-1α were used and the expected 49 kDa PfEF-1α band was found in both the wild type and pfpmtΔ strains (FIG. 8E). Immunofluorescence analysis confirmed the loss of PfPMT expression in the pfpmtΔ clone (FIG. 8F).

To determine whether PfPMT encodes the only phosphoethanolamine methyltransferase activity of *P. falciparum*, the three-step methylation of phosphoethanolamine to phosphocholine was examined in protein extracts from either wild type or pfpmtΔ parasites using radiolabeled S-adenosyl methionine (SAM) as a methyl donor. As a control, we constructed a pfpmtΔ+PfPMT complemented strain, by expressing wild type PfPMT episomally in the pfpmtΔ strain. Whereas the formation of radiolabeled phosphocholine was readily detectable in reactions with extracts from the wild type and pfpmtΔ+PfPMT strains, radiolabeled phosphocholine was not detected in the reaction mixture containing extracts from the pfpmtΔ parasites (FIG. 9A). Together, these results confirmed the loss of PfPMT enzymatic activity in the pfpmtΔ parasites and demonstrated that PfPMT encodes the only phosphoethanolamine methyltransferase activity in *P. falciparum*.

To determine how loss of PfPMT affected the SDPM pathway for the synthesis of PtdCho, in vivo labeling assays with [$^{14}$]-Ethanolamine in the wild type, pfpmtΔ+PfPMT and pfpmtΔ strains were performed in medium lacking choline. Two-dimensional thin layer chromatography (TLC) analysis of the parasite phospholipids following incubation with [$^{14}$]-Ethanolamine revealed, as expected, the formation of radiolabeled PtdEtn in all three parasite strains (FIG. 9B, top panels). In contrast, the formation of radiolabeled PtdCho from [$^{14}$C]-Ethanolamine was only detectable in the wild type and pfpmtΔ+PfPMT parasites, not in the pfpmtΔ strain (FIG. 9B, top panels). Thus disruption of PfPMT function results in a complete loss of the SDPM pathway. This result also confirms that *P. falciparum*, unlike mammalian and yeast cells, cannot form PtdCho from PtdEtn. Labeling with [$^{14}$]-Choline resulted in the incorporation of this substrate into phosphatidylcholine in all three strains (FIG. 9B, bottom panels), demonstrating that the CDP-choline pathway is not altered upon the loss of PfPMT.

Example 10

Effect of Loss of PfPMT Function on Intraerythrocytic Life Cycle of pfpmtΔ Parasites To examine the importance of PfPMT in the *P. falciparum* intraerythrocytic life cycle, the growth rate of pfpmtΔ parasites during their asexual development and multiplication within human erythrocytes was compared to that of the wild-type and pfpmtΔ+PfPMT strains. Since the SDPM and the CDP-choline pathways converge at the synthesis of p-Cho from p-Etn and choline, respectively, it was proposed that choline supplementation could complement any defects resulting from the loss of the PfPMT gene.

The three strains were synchronized, and cultured at 1% parasitemia in media containing increasing concentrations of choline for 48 hours; parasites were monitored by measuring the production of parasite-specific lactate dehydrogenase (LDH) (Makler et al., 1993 Makler, M. T., et al. (1993), *Am. J. Trop. Med. Hyg.* 48, 739-741) as well as by Giemsa-based microscopic morphological analysis (FIG. 10). While similar parasite counts were found in the wild type and pfpmtΔ+ PfPMT strains, the parasitemia in the pfpmtΔ culture was lower by at least 50% at choline concentrations of 0, 10 and 50 µM (FIGS. 10A and 10B). Addition of choline at 200 or 500 µM (10- and 25-fold higher than the physiological level, respectively) only partially complemented the growth defect (FIGS. 10A and 10B).

Wild type and pfpmtΔ+PfPMT parasites inoculated at 3% starting parasitemia and cultured for two consecutive generations in medium lacking choline increased their parasitemia to ~35%, whereas pfpmtΔ parasites reached only 10% parasitemia under the same conditions (FIG. 10C). These results indicated that choline supplementation at physiological levels could not rescue the loss of PfPMT, though a marginal rescue effect was notable at concentrations that were at least 10-fold the physiological level.

Microscopic analysis of highly synchronized cultures indicated that, whilst the wild type and the pfpmtΔ+PfPMT strains progressed normally, the pfpmtΔ strain formed trophozoites and schizonts that were smaller in size and depicted delayed progression rate (FIGS. 11A and B). Determination of the relative size of the mature schizonts by measuring the average RBC area occupied by the parasites showed that mature schizonts of the pfpmtΔ parasites occupied only about 33% of the RBC area whereas their wild type and pfpmtΔ+ PfPMT counterparts occupied ~75% of the RBC area, (FIG. 11B).

Quantitative analysis of the trophozoite parasite stage by light microscopy following Giemsa staining of parasites cultured in the absence or presence of different concentrations of choline revealed that 48%, 53%, 59% and 59% of the wild type trophozoites grown in medium with 0, 50, 100 and 200 µM choline, respectively, occupied ~60% of the area of the host erythrocyte 32 hours post-invasion. On the other hand, only 8%, 10%, 12% and 12% of the pfpmtΔ trophozoites in culture showed similar morphology at choline concentrations of 0, 50, 100 and 200 µM, respectively (FIG. 12). The remaining percentage of trophozoites in both cases occupied 40% of the RBC area (FIG. 12). These results suggest that PfPMT plays an important role in parasite's intraerythrocytic development.

Example 11

Effect of Loss of PfPMT Function on DNA Replication of pfpmtΔ Parasites

The low number of daughter parasites produced during the intraerythrocytic life cycle of pfpmtΔ could be due to a low number of nuclei produced during schizogony (and thus a low number of merozoites). Therefore, nuclear division in wild type, pfpmtΔ and complemented strains was examined. This was achieved by synchronizing the three parasite strains, collecting samples every 2 hours for 12 h, with the first sample collected prior to parasites' entry into schizogony, staining parasite nuclei and determining the number of nuclei per red blood cell by flow cytometry. Stained wild type and pfpmtΔ+PfPMT infected erythrocytes showed a gradual increase in the percent of cells with more than one nucleus from 2-3% to 11-13% in 12 hours (FIG. 13B-E). In contrast, the number of pfpmtΔ-infected erythrocytes containing more than one nucleus did not significantly increase during the 12 hours following the start of nuclear division (FIG. 13C). The uninfected red blood cells did not show any increase in intensity above the established baseline (FIG. 13A).

To examine this defect further, we quantified the number of nuclei from synchronized populations of live pfpmtΔ and pfpmtΔ+PfPMT parasites under continuous perfusion using DNA targeted fluorophores and Spinning Disc Confocal Microscopy (SDCM). The complemented strain (FIG. 14A) showed a Gaussian distribution of numbers of new nuclei per schizont that is similar to that measured previously for wild type parasites (Gligorijevic, B. et al. (2008), supra). In contrast, the pfpmtΔ strain grown in the absence of exogenous choline (FIG. 14B) showed a distinctly biphasic distribution of nuclei counts with the majority of schizonts showing a reduced number of nuclei consistent with microscopic and flow cytometric analyses, consistent with the microscopic and flow cytometric analyses. Interestingly, when the pfpmtΔ strain was grown in the presence of exogenous choline, (FIG. 14C) the distribution remained broadened, but shifted to higher numbers of nuclei. These results suggest that efficient production of phosphocholine is essential for formation of new nuclei during schizogony.

Example 12

Effect of Loss of PfPMT Function on Cell Viability of pfpmtΔ Parasites

To assess the effect of PfPMT disruption on the viability of intraerythrocytic parasites, asynchronous wild type, pfpmtΔ+ PfPMT and pfpmtΔ parasites were analyzed by TUNEL (TdT-mediated dUTP-X nick end labeling) assay, which measures DNA fragmentation resulting from cell death. Whereas pfpmtΔ parasites cultured in the absence or presence of 20 or 200 µM choline showed substantial degrees of TUNEL-positivity whereas wild type and pfpmtΔ+PfPMT parasites cultured under similar conditions did not reveal any TUNEL-positive parasites (FIG. 15A). Wild type parasites treated with DNase I to induce chromosomal DNA strand breaks stained positively in the presence of the TdT enzyme (FIG. 15B) but negatively when TdT enzyme was omitted from the reaction (FIG. 15A).

To determine that TUNEL positive cells correspond to dead parasites, wild type, pfpmtΔ+PfPMT and pfpmtΔ parasites were treated with 100 nM chloroquine or 100 nM pyrimethamine (concentrations ~10-fold above their $IC_{50}$) for 24 h and subjected to the TUNEL assay. In all cases, the drug-treated parasites were positively stained with TUNEL (FIG. 15C). Taken together, these results suggest that PfPMT is critical for parasite's viability. It has been shown that *P. falciparum* parasites lacking PfPMT are unable to synthesize their major phospholipid, PtdCho, via the SDPM pathway, and display severe alterations in parasite development, multiplication, survival and infectivity. These results suggest that PfPMT plays a key physiological role during the intraerythrocytic life cycle of the parasite, a property that allows the development of novel antimalarial drugs and vaccines.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

falciparum FCH/4 (Philippines) strain, falciparum Santa Lucia (Salvador I) strain and falciparum Malayan Camp (MC) strain.

4. The composition of claim 1, wherein the malarial parasite comprises a second non-functional gene that, when present in naturally occurring form, encodes a protein necessary for continued in vivo survival, proliferation, and/or infection of host red blood cells by the parasite.

5. The composition of claim 4, wherein the second non-functional gene is PfNT1.

6. The composition of claim 1, further comprising an adjuvant.

7. A method of eliciting an immune response in a host, comprising introducing into the host an effective amount of a composition comprising a human malarial parasite with at least one gene that has been rendered non-functional, wherein the at least one non-functional gene is a *Plasmodium* phosphoethanolamine methyltransferase (PMT) gene, and wherein the composition is introduced in an amount sufficient to elicit an immune response.

8. The method of claim 7, wherein the composition is administered to the host by injection.

9. The method of claim 7, wherein the composition is administered to the host by injection of the composition on multiple days.

10. The method of claim 7, wherein the composition is administered with an adjuvant.

What is claimed is:

1. A composition for eliciting an immune response in a host, comprising a human malarial parasite with at least one gene that has been rendered non-functional and a pharmaceutically acceptable carrier, wherein the at least one non-functional gene is a *Plasmodium* phosphoethanolamine methyltransferase (PMT) gene.

2. The composition of claim 1, wherein the malarial parasite is selected from the group consisting of *Plasmodium vivax, Plasmodium malariae, Plasmodium ovale*, and *Plasmodium falciparum*.

3. The composition of claim 1, wherein the malarial parasite is a strain of *P. falciparum* selected from the group consisting of falciparum 3D7 strain, falciparum Vietnam-Fort (FVO) strain, falciparum Uganda-Palo Alto (FUP) strain, 11. The composition of claim 1, further comprising one or more additional malarial parasites each with at least one gene that has been rendered non-functional, wherein the non-functional gene, when present in naturally occurring form, encodes a protein necessary for continued in vivo survival, proliferation, and/or infection of host red blood cells by the parasite, and wherein the one or more additional malarial parasites are selected from the group consisting of *Plasmodium vivax, Plasmodium malariae, Plasmodium ovale* and *Plasmodium falciparum*.

12. The composition of claim 11, wherein the one or more additional malarial parasites are one or more strains of *P. falciparum* selected from the group consisting of falciparum 3D7 strain, falciparum Vietnam-Fort (FVO) strain, falciparum Uganda-Palo Alto (FUP) strain, falciparum FCH/4

(Philippines) strain, falciparum Santa Lucia (Salvador I) strain and falciparum Malayan Camp (MC) strain.

13. A method of producing a composition for eliciting an immune response in a host, comprising the steps of:
   (a) preparing an attenuated human malarial parasite by using knockout technology or homologous recombination technology to render at least one gene of the malarial parasite non-functional, wherein the at least one gene is a *Plasmodium* phosphoethanolamine methyltransferase (PMT) gene;
   (b) growing and propagating the attenuated malarial parasite using a growth medium comprising a higher than physiological concentration of one or more essential nutrients; and
   (c) isolating the attenuated parasite from the growth medium,
   wherein the composition comprises the attenuated parasite.

14. The method of claim 13, further comprising the step of:
   (d) exposing the isolated attenuated malarial parasite to a medium comprising physiological concentrations of essential nutrients for a predetermined length of time.

15. The method of claim 13, wherein the preparation of the attenuated malarial parasite further comprises using knockout technology or homologous recombination technology to render nucleoside transporter 1 (NT1) non-functional.

* * * * *